United States Patent [19]

Palmer et al.

[11] Patent Number: 5,032,506

[45] Date of Patent: Jul. 16, 1991

[54] COLOR CONTROL SYSTEM

[75] Inventors: John L. Palmer, Philadelphia; Marsha W. Timmerman, Allentown, both of Pa.

[73] Assignee: Enzymatics, Inc., Horsham, Pa.

[21] Appl. No.: 942,414

[22] Filed: Dec. 16, 1986

[51] Int. Cl.$^5$ .................. C12Q 1/32; C12Q 1/26; C12N 11/12
[52] U.S. Cl. ................ 435/26; 435/25; 435/4; 435/174; 435/175; 435/176; 435/177; 435/178; 435/179; 435/805; 435/810
[58] Field of Search .............. 435/25, 26, 175, 176, 435/177, 178, 179, 805, 810, 4

[56] References Cited

U.S. PATENT DOCUMENTS 4,629,697  12/1986  Limbach et al. .................. 435/26

OTHER PUBLICATIONS

Barman, T. E. "*Lipoamide Dehydrogenase*" in *Enzyme Handbook*, vol. 1, pp. 203-204, (1969).

Primary Examiner—Esther L. Kepplinger
Assistant Examiner—Toni R. Scheiner
Attorney, Agent, or Firm—Finnegan, Henderson, Farabow, Garrett & Dunner

[57] ABSTRACT

An assay system useful for the determination of NAD(P)H, NAD(P), or a substrate of an enzyme which reacts with the formation or comsumption of NAD(P)H. Concentrations of organic substrates for example alcohol, cholesterol, uric acid, in a biological fluid such as saliva, blood or urine may be determined. The system includes a diaphorase which catalyzes a NAD(P)H-dependent reduction of a chromogen to cause a visible color change; this color change is indicative of the concentration sought to be determined. The system includes a chromogen which is a first substrate for the diaphorase which causes a color change when reduced by NAD(P)H, and a second substrate which is a competing substrate for the diaphorase; the competing substrate is irreversibly reduced by the diaphorase. The system is capable of measuring colorimetrically without dilution concentrations of organic compounds in biological fluids which previously could not be measured in such concentration. The system provides a convenient, practical sobriety test. The invention also provides a method for such determination and diagnostic kit.

61 Claims, 13 Drawing Sheets

COLOR IS LINEARLY RELATED TO NADH OVER A RANGE FROM 0 M NADH TO A POINT WHERE EITHER THE CHROMOGEN OR THE SECOND SUBSTRATE IS EXHAUSTED

COLOR CONTROL SYSTEM

BACKGROUND OF THE INVENTION

The present invention relates to a colorimetric determination of biological molecules or organic compounds that are substrates for NAD(P)-linked dehydrogenase enzymes. In addition, this invention is useful for the colorimetric determination of the levels or concentrations of NAD(P) linked dehydrogenase enzymes. This invention is also useful in the direct colorimetric measurement of NAD(P) and NAD(P)H.

This invention reduces the amount of color that is generated when the substances are assayed which cause color to be generated in the presence of a chromogen. This reduction in color generation greatly expands upward the possible concentration of substance that can be measured. This makes possible the determination of the concentration of a wide variety of medical and industrial substances without dilution of the aqueous sample containing that substance to lower the concentration of the substance to be measured. This reduction in color that is generated in response to NADH production into a visible (or readable) range, is unknown in the prior art.

THE INVENTION AND PRINCIPAL OBJECTS OF THE INVENTION

The invention provides an improved system, devices and method for measuring qualitatively and quantitatively the concentration of NAD(P)H or NAD(P) using an enzyme, a diaphorase (lipoamide dehydrogenase), a chromogen which acts as a substrate (generally herein called a "first substrate") for the diaphorase, which generates color when reduced by NAD(P)H and a second substrate for the diaphorase, which substrate is irreversibly reduced but generates no color, at least not in the color range in which the chromogen generates color.

The invention is operative in two different ways to generate the color corresponding to the amount of material sought to be determined: by the development of color (from colorless to color) or by the reduction of color from a high color intensity to a lower color intensity within the visible and readable range. Generically therefore, the method of the invention relates and refers to "color change".

An unique feature of the invention is that there is generated less than 1 equivalent of colored dye from the chromogen per mole of NAD(P)H.

The invention also provides for the measurement of an organic compound, generally in a biological fluid sample which in the presence of dehydrogenase is oxidized to yield NAD(P)H. Thus, the concentration of alcohol, sugar, ketones or other organic compounds can be readily measured in various concentrations without dilution, as is the conventional practice.

In accordance with the process of this invention, a competing substrate is reduced by diaphorase in the presence of NADH while concurrently the chromogen is likewise reduced so that for each mole of NADH present or (produced from another substrate) there is produced an equivalence of color less than the equivalence of NADH.

DESCRIPTION OF PRIOR ART

Figure 1:
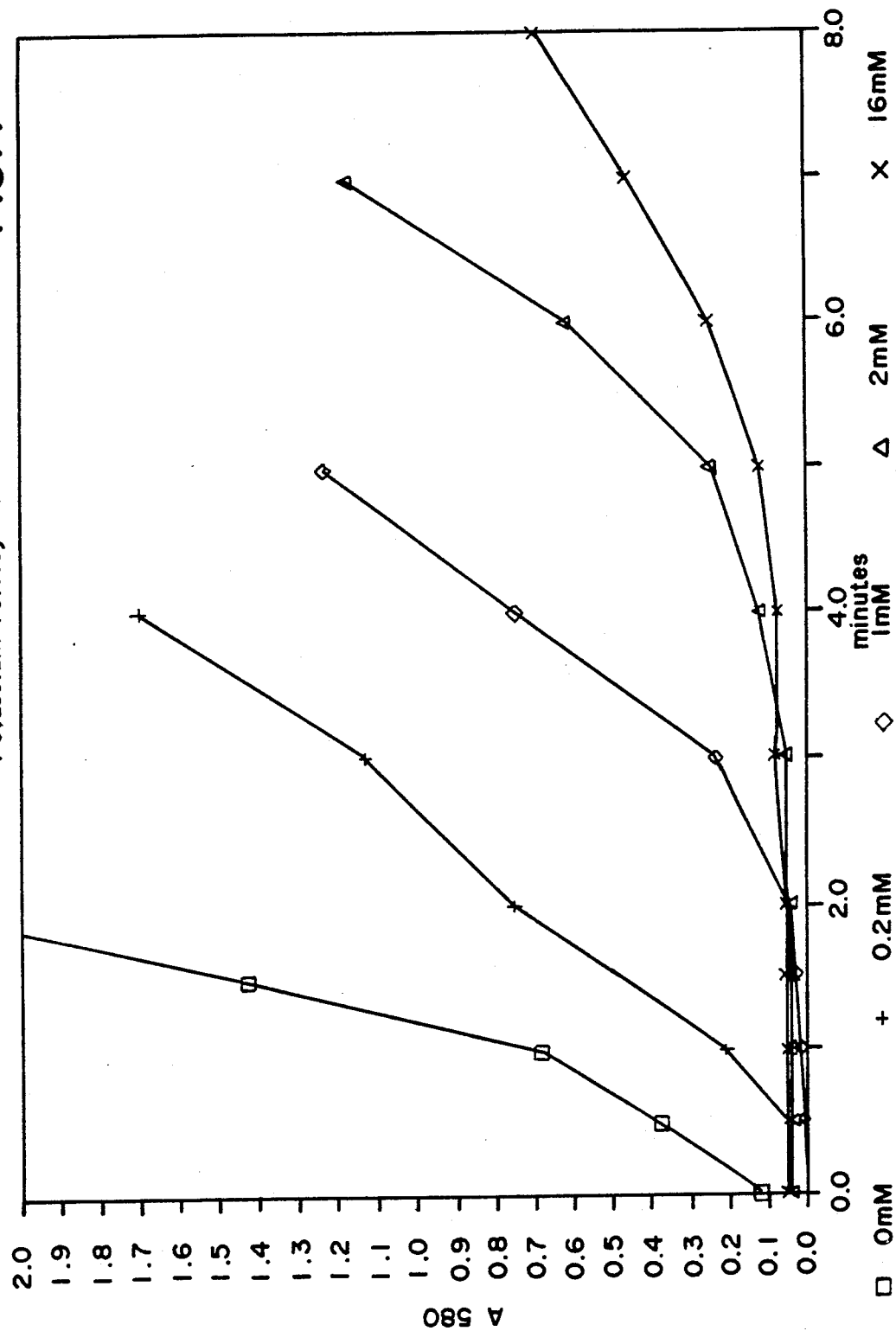
FIG. 1 is a graph which shows the rate of color generated in the diaphorase competing substrate test by potassium ferricyanide at different concentrations during the time shown.

This invention makes use of an enzyme that has been variously called diaphorase or lipoamide dehydrogenase (hereafter called diaphorase). Diaphorase is the generic name for any enzyme that catalyzes the NAD(P)H reduction of dyes or chromogens (prodyes) to produce color changes. Diaphorase seems to be ubiquitous in that it is found in both eukaryotic and prokaryotic organisms. The enzyme that is from eukaryotic and aerobic prokaryotic organisms has been well studied and shown to be the lipoyl dehydrogenase subunit of pyruvate dehydrogenase and alpha-ketogluterate dehydrogenase (V. Massay, Biochem. Biophys. Acta., 37 314–322 [1960]). Massey studied the substrate specificity of lipoyl dehydrogenase and showed that the enzyme reduces a wide variety of lipoic acid derivatives, for example: DL-lipoic acid, DL-lipoyl glycine, DL-lipoyl-beta-alanine, DL-lipoyl glycylglycine, DL-carboethoxy lipoanilide, DL-lipoanilide, and DL-lipoamide, in addition to potassium ferricyanide. The enzyme from an aerobic prokayrotes, for example the commonly used enzyme from *Clostridium kluyverii*, is of unknown biological function. Diaphorase and lipoyl dehydrogenase have been reviewed (U. Schmidt, P. Graffen, K. Altland & H. W. Goedde, Advances in Enzymology, 32 423–469 (1969) and C. H. Williams, The Enzymes, 13 106–219 (1976).

These publications are incorporated herein by reference especially for (but not only for) their disclosure of lipoic acid derivatives or compounds suitable for use in the invention and for the diaphorases.

The use of diaphorase to produce changes in visible color is widely discussed in the literature. Indeed, one of the first assays for this enzyme involved the reduction of 2,6-dichlorophenolindophenol (DCPIP) by NADH. DCPIP is a dye, while reduced DCPIP is colorless. Boethling and Weaver (R. S. Boethling and T. L. Weaver, Clin. Chem., 25 2040–2042 [1979]) report a diaphorase assay which utilizes the prodye, thiazolyl blue tetrazolium bromide. Upon reduction, this colorless molecule is converted into a colored formazan which has a maximum absorbence at 560 nm.

The tetrazolium salt 3-p-nitrophenyl-2-iodophenyl-5-phenyltetrazolium (INT) and diaphorase were used in production of an automated assay for urinary lactate dehydrogenase (N. J. Hella and S. Weinhouse, Anal. Biochem., 13, 322–325 [1965]), and in the development of a single-step assay for serum lactate dehydrogenase (C. C. Allain, D. P. Henson, M. K. Nadel, and A. J. Knoblesdroff, Clin. Chem., 19, 223–227 [1973]). The colorimetry of diaphorase and the preparation of clinical chemical reagents has been discussed (F. J. Gella, M. T. Olivella, F. Pegueroles, and J. Gener. Clin. Chem., 27, 1686–1689 [1981]).

The use of diaphorase in colorimetric assays has also been discussed in the patent literature. U.S. Pat. No. 4,556,634 describes the use of formic acid lower alkyl esters to stop a reaction containing dehydrogenase, diaphorase, NAD(P), and tetrazolium salt. In this patent, the amount of dehydrogenase is inferred from the amount of formazan dye produced in a given, carefully measured time.

U.S. Pat. No. 4,427,771 discloses an assay method for amylase activity and a method of producing maltose dehydrogenase for use therein. In this patent, a sample of serum, saliva or urine is pretreated with alpha-glucosidase, hexokinase, and ATP to remove glucose and maltose. A glucose polymer is added to the sample, along with maltose dehydrogenase, NAD or NADP, and diaphorase and a tetrazolium salt or phenazinemethosulfate and a tetrazolium salt. The amylase breaks down the glucose polymer to form maltose. The maltose is oxidized by maltose dehydrogenase to form NADH or NAD(P)H, which then reacts with the tetrazolium salt to produce a colored dye.

U.S. Pat. No. 4,351,899 describes the use of a test surface containing the dried residue resulting from the impregnation of the surface with a tetrazolium salt, NAD, a dehydrogenase, and a electron carrier. In this patent, diaphorase is not used. Instead, the electron carrier meldola blue is used to catalyze the transfer of electrons from NADH to the tetrazolium salt. Meldola blue is also used as an electron carrier in U.S. Pat. No. 4,254,222, which discusses the assay of lactic acid and beta-hydroxybutyrate via the dehydrogenases lactic dehydrogenase and beta-hydroxybutyrate dehydrogenase.

U.S. Pat. No. 4,271,265 describes the use of diaphorase or electron transfer agents, tetrazolium salts, and NADP in the assay of glutamate-oxalacetate transaminase and glutamate-pyruvate transaminase.

U.S. Pat. No. 4,247,633 describes the production of a dried, all-in-one reagent for the assay of creatine phosphokinase. This dried reagent contains: ADP, creatine phosphate, magnesium ions, glucose, hexokinase, NAD or NADP, INT, diaphorase, buffer, reduced glutathione, and AMP.

U.S. Pat. No. 4,223,090 describes reagents for the enzymatic determination of triglycerides. These reagents consist of a lipase, which hydrolyzes the triglycerides to produce glycerol; glycerol dehydrogenase, buffer and NAD, which oxidize the glycerol to produce NADH; and diaphorase and a tetrazolium salt, which uses the NADH to produce a colored formazan dye and regenerate NAD. The improvement described in this patent in the inclusion of manganese ion which is present at concentrations from 0.05 to 0.15 mM.

U.S. Pat. No. 4,215,197 describes the test means and method for creatinine determination. In this patent, creatinine is enzymatically hydrolyzed to creatine. The creatine is further enzymatically hydrolyzed to sarcosine and urea, and the sarcosine is enzymatically converted to formaldehyde and glycine with the production of NADH. The NADH then reduces the tetrazolium salt, MTT, either directly or via diaphorase to produce a colored dye. The patent also describes the production of a dried reagent tablet containing the described ingredients.

U.S. Pat. No. 4,142,938 describes a method for the determination of triglycerides and glycerol. In this patent, triglycerides are hydrolyzed by sodium hydroxide treatment at moderate heat. The resulting glycerol is then removed from interfering substances by treatment with magnesium ions, which precipitates the interfering substances. The sample is centrifuged to remove the precipitate and the supernatant is assayed for glycerol content in a liquid enzymatic reaction containing: ATP, glycerol kinase, glycerol-1-phosphate dehydrogenase, NAD, diaphorase, and a tetrazolium salt. The glycerol is converted to glycerol-1-phosphate by ATP in a reaction catalyzed by glycerolkinase. The glycerol-1-phosphate is then oxidized to form NADH and glyceraldehyde-3-phosphate. The NADH is then used to reduce the tetrazolium salt in a diaphorase catalyzed reaction.

U.S. Pat. No. 4,024,021 describes a method for the determination of glutamate and glutamic transaminases in biological fluids. In this patent, substrates for the transaminases are incubated with the transaminases so that glutamate will be produced. The glutamate produced is oxidized by glutamate dehydrogenase in the presence of NAD to produce alpha-oxoglutarate, ammonia, and NADH. The NADH is then reacted with the tetrazolium salt, INT, to produce a colored formazan. This last reaction can be catalyzed either by diaphorase or by the electron carrier, N-methyl phenazonium methosulfate. The intensity of the formazan color produced per unit time is measured to give a measurement of the transaminase activity.

U.S. Pat. Nos. 3,867,259 and 3,867,258 describe the production of lactate dehydrogenase test material. The test material consists of a bibulous material containing the dried residue resulting from the impregnation of the material with a tetrazolium salt, a chromatographic effect preventor, an antioxidant, diaphorase, NAD, and an alkali lactate salt mixture. U.S. Pat. No. 3,867,258 discloses the use of diaphorase immobilized to a hydrophilic, cross-linked, sulfited aldehyde or ketone polymer dispersed throughout the interstices of the material. In these patents, lactate dehydrogenase from sera oxidizes the lactate to pyruvate with the concomitant conversion of NAD to NADH. The diaphorase in the material then catalyzes the NADH dependent reduction of the tetrazolium salt to form a colored dye. As diaphorase is present in excess over the lactate dehydrogenase to be assayed, the rate of color formation (the amount of color produced in a unit time) is an indicator of the lactate dehydrogenase concentration in the sera sample.

U.S. Pat. No. 3,791,931 also discusses a reagent and method for the determination of lactate dehydrogenase. This invention uses pig heart diaphorase obtained from the protein fraction of a pig's heart insoluble in 1.6 to 2.8M ammonium sulfate by treating the insoluble protein fraction with 0.1–0.3% w/v polyethyleneimine, heating at 70 to 80 degrees C, absorption on a weakly acidic cation exchanger and subsequent elution. This patent also discusses the use of a buffer, a stabilizer, and bovine serum albumin (BSA) in the aqueous assay of lactate dehydrogenase.

In none of the above patents, or in the scientific literature, is there discussed a method of controlling the amount of color that is generated by diaphorase and NADH or NAD(P)H. Indeed, in all of the above patents, one equivalent of dye is produced for every equivalent of NAD(P)H that was present in or produced in the environment as by the oxidation of the substrate. This one-to-one ratio between NAD(P)H and dye produced, imposes serious disadvantageous constraints upon all of the above, previously disclosed methods.

The nature of the problem confronting those skilled in the art may be presented as follows. The vast majority of dyes have millimolar extinction coefficients between 5 and 25 O.D. units. This large absorbence makes it necessary to dilute many medical samples before assay. For example, blood and saliva alcohol concentration can range up to 75 mM while the legal value of 0.1% is 22 mM. Beta-hydroxybutyrate, the major constitute of blood ketones, can be observed in concentrations up to 20 mM, and blood cholesterol concentrations vary from 2 to 10 mM. At a 10 mM concentration of test material, dye with a mM extinction coefficient (E-mM) of 5 will produce a solution with an absorbency of 50 O.D. units per cm; a dye with a E-mM of 20 will result in a solution with an absorbency of 200 units per cm. The eye cannot distinguish color difference above 1.5 absorbency units and even the best spectrophotometers cannot differentiate color differences when the solution has an absorbence greater than 3 units.

In the current art, when dehydrogenase/diaphorase assays are used, the sample is diluted so that the concentration of the test material will produce a color within the readable range. This dilution can be either done by hand, or it can be automated as it is currently done in many instruments located in clinical assay laboratories. This requirement for dilution has prevented the production of easy-to-use colorimetric devices for the assay of many biological molecules, such as kits which could be used on location.

Indeed, the scientific and patent literature is surprisingly devoid of attempts at reducing the color that is generated in the assay of biological molecules. However, the problem referred to above has not gone totally unnoticed. U.S. Pat. No. 4,490,465 is a patent that is concerned with reducing the amount of color that is generated in the measurement of biological molecules. This patent discloses a method for reducing the one-to-one ratio of NADH to dehydrogenase substrate that is seen in NAD(P) dehydrogenase reactions. The method disclosed in this patent does not (as does the present invention) reduce the one-to-one ratio of dye produced to NAD(P)H produced from NAD(P).

The method disclosed in this earlier patent is considerably different from, and has serious disadvantages in comparison with the method of the invention discussed herein. The previous patent contacts a molecule to be assayed, (A), with two different enzymes that will react with this molecule. One of these enzymes is a dehydrogenase and the other is an oxidase:

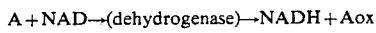

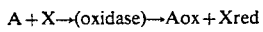

wherein X equals flavin, oxygen, non-NAD electron acceptor. Therefore, at any given concentration of (A) less than one equivalent of NADH is produced. This NADH can be converted into a color by standard methods, for example by the use of diaphorase and tetrazolium salts as has been previously discussed above, to result in the generation of less than one equivalent of dye per mole of (A), the dehydrogenase substrate. It is a key aspect of that patent as the patentee notes, that the same—the single—substrate is converted by the several enzymes into different products.

The disadvantages of this two enzyme approach are the following: (i) a straight line is not obtained when color is plotted against concentration of (A) (as shown by the patentees); and (ii) as the assay device ages on the shelf or in shipping the ratio of dehydrogenase to oxidase enzyme activity will vary due to differing rates of denaturation of these two enzymes. It is the relative activities of these two enzymes that determine the ratio of NAD(P)H produced to substrate consumed. Therefore, the amount of color that is generated at a given concentration of (A) will change with shelf life. This disadvantage renders it impossible to utilize this known technology to produce a device that will reproducibly generate a set color at a set concentration of substrate to be assayed. This serious disadvantage is an unsolvable problem with this known approach.

DETAILED DESCRIPTION OF THE INVENTION

The invention is useful in the colorimetric determination of NAD(P) or NAD(P)H, a dehydrogenase substrate, or a dehydrogenase enzyme. All of these molecules bear a set relationship to the concentration of NAD(P)H, as will be further disclosed below. Solely for ease in reference in the following section, the discussion will refer to the concentration of NAD(P)H but the usefulness of this invention applies equally well to the detection and assay of all of these molecules.

It has been found in accordance with the invention that the color produced by the diaphorase from the reduction of the chromogen is markedly reduced in the presence of a second substrate for the diaphorase. In accordance with the invention, one of these substrates is a chromogen, and the other substrate is a molecule that irreversibly accepts electrons from the NAD(P)H (the "competing substrate") in a diaphorase catalyzed reaction. With this dual substrate system, it was hoped that the amount of color produced at any given concentration would be reduced and would be at a ratio of less than one molecule of dye per molecule of substrate.

In earlier work, potassium ferricyanide ($K_3FeCN_6$) was first considered as the competing substrate and a tetrazolium salt as the chromogen. There was every reason to believe that this combination would work. $K_3FeCN_6$ is a well known substrate for diaphorase, the reduction of this compound was expected to be irreversible. Further, the affinity of these pairs of substrates for the enzyme, as measured by the substrate Km, is generally within the same range. Massey (Biochem. Biophys. Acta. [1960], 37, 314–322) has disclosed that the Km of $K_3FeCN_6$ is 0.27 mM, while F. J. Gella et al (F. J. Gella, M. T. Olivella, F. Pegueroles, and J. Gener, Clin. Chem. [1981], 27, 1686–1689) has disclosed that the Km for the tetrazolium salts are: 0.87 mM for INT, 1.25 mM for MTT (thiazolyl blue tetrazolium bromide), and 2 mM for NBT (nitro blue tetrazolium chloride).

Therefore, it was a surprise to find that this system did not work as was expected. In further work, it was found that the $K_3FeCN_6$ was preferentially reduced until it was exhausted, and only then was the tetrazolium salt chromogen reduced to produce color. From this work it was concluded that the two substrates did not share random access to the diaphorase activities. Therefore, in cases where the concentration of $K_3FeCN_6$ was greater than the concentration of NAD(P)H assayed, no color was produced in the system. In cases where the NAD(P)H concentration was greater than the concentration of $K_3FeCN_6$, the final color was that calculated by subtracting the concentration of $K_3FeCN_6$ for that of the NAD(P)H and multiplying the resulting number by the known extinction coefficient of the reduced tetrazolium chromogen.

In further work, the use of 1,4-benzoquinone as a competing substrate was considered. Benzoquinone has never before been implicated as a substrate for diaphorase, so this choice may have seemed illogical, but it was reasoned that this molecule was antiaromatic, and easily reduced. Therefore, it seemed a reasonable candidate substrate. It was found that benzoquinone is indeed a substrate for diaphorase. However, benzoquinone behaved like $K_3FeCN_6$ and gave identical results. That is, no color was generated by the system until the benzoquinone was exhausted.

In additional work, the definitional requirements for an ideal second or competing substrate for the purpose of a main embodiment of the invention were discovered. A second substrate is in accordance with these findings, a compound which meets a three-way test.

The first requirement for the substrate is that it be or caused to be an irreversible substrate for the diaphorase. In accordance with the invention, the reduction of the competing substrate should be irreversible. This property can be determined as follows.

Diaphorase is mixed with a concentration of NAD(P)H capable of producing a dark color, for example 2 mM; a concentration of tetrazolium salt chromogen that is greater or equal to the concentration of NAD(P)H, for example 4 mM, and a suitable concentration of test candidate substance, for example, from 1 to 500 mM. These reagents are allowed to react to completion, and the end point color is determined. When the second substrate is an irreversible substrate for diaphorase, the color that is generated at end point in the presence of that competing substance, will be less than that generated in a control tube wherein the competing substance is omitted.

Figure 2:
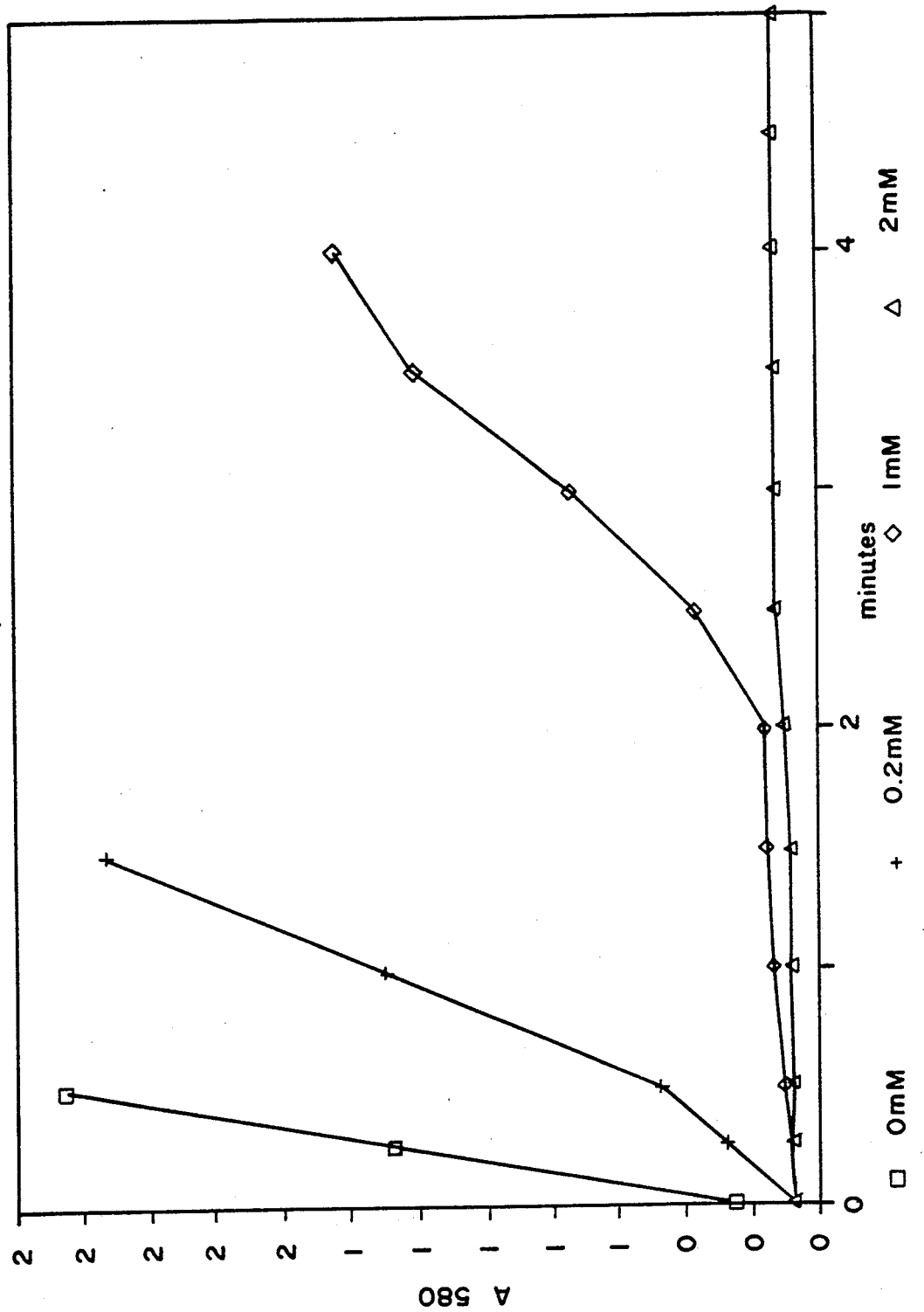
FIG. 2 is a graph which shows the rate of color generated in the diaphorase competing substrate test by benzoquinone at different concentrations during the time shown.

The second requirement for a suitable second substrate to be used in accordance with the invention is that the color generated by the chromogen must be at a non-zero initial rate when the second substrate is present in sufficient quantities to inhibit the diaphorase. This property is determined as follows: diaphorase was mixed with a quantity of NAD, for example 0.1 to 25 mM; an excess of dehydrogenase enzyme, for example alcohol dehydrogenase; a large excess of concentration of a substrate for the dehydrogenase enzyme, for example alcohol at a concentration of between 10 and 1,000 mM; a tetrazolium salt chromogen, for example MTT at 2 mM; and the second or competing substrate at a concentration of between 4 and 500 mM. The entire reaction mixture is placed in a spectrophotometer, and the kinetics of color production measured. A suitable second substrate is one which causes a color generation at a non-zero rate, that is less than the rate that is seen in the absence of the competing substrate. Suitable second substrates are described further below.

Where a rate of zero color production was observed until the competing substrate was exhausted, and only then color produced, the competing substrate does not qualify for the purpose of this embodiment of the invention. Such was the result for both $K_3FeCN_6$ and 1,4-benzoquinone as disclosed in FIGS. 1 and 2 presented and discussed herein.

The third requirement for a suitable substrate candidate is that the amount of color that is generated at each of several concentrations of NAD(P)H is linearly related to that concentration. In this third test, diaphorase is mixed with several different concentrations of NAD(P)H, for example between 0 and 100 mM; a concentration of chromogen, for example INT at 2 mM; and a concentration of competing substance that is greater than the highest concentration of NAD(P)H utilized, and is constant throughout the test.

These reactions were set up in several different test tubes, each tube containing a different concentration of NAD(P)H and the reaction allowed to go to completion. The color that is generated at each NAD(P)H concentration is measured and plotted against the concentration of NAD(P)H that was in that sample. Competing substances—suitable substrates—will only pass this test if this test yields a straight line over at least a section of the NAD(P)H concentrations.

There are therefore in accordance with the invention, two main embodiments: a first wherein the affinity of the enzyme (the diaphorase) for the two substrates is within approximately or within the same range of magnitude; a second embodiment wherein the diaphorase has a greater affinity for the competing substrate than for the other substrate. In the first embodiment, the color generated by the chromogen is at a non-zero initial rate; in the second, the rate of color production from the chromogen is nil until the competing substrate is totally (or virtually) totally reduced.

The relative mole percent of chromogen to competing substrate useable in accordance with the invention, varies over a wide range. One skilled in the art can determine readily the optimum relative proportions of the two substrates for the diaphorase. It is evident that the relative amounts of the two substrates will vary depending on the intensity of the colored dye generated by the chromogen in the absence of the competing substrate. If the chromogenic substrate is such that it would not generate a very large excess of dye beyond that which can be readily colorimetrically measured, the proportion of competing substrate that needs to be present is in a smaller proportion than if the chromogen is such as to generate a larger or intenser excess of color determinable colorimetrically. Likewise the relative proportions will depend on the nature of the substrate and the amount of the substrate in solution which is sought to be determined. In general, the proportion of competing substrate is at least that much as will cause a decrease in the amount of colored dye generated by the diaphorase reaction on the chromogen. The maximum of competing substrate should not be such as to cause the amount of colored dye generated to be so small as not to be measured colorimetrically. The relative molar proportion of competing substrate to chromogen and vice versa is also dependent on the amount of NAD(P)H present in the reaction. The amount of NAD(P)H present should be enough to cause the reduction of both the chromogen and the competing substrate. In general, the relative molar proportion of competing substrate to chromogen ideally should be at a ratio equal or greater to 1 to 1 but either one of the substrates may vary and be in excess of the other under certain circumstances, ranging to a ratio greater than 400 to 1 with respect to the other, and depending on the amount of color reduction required. In general, though, an excess of chromogen over competing substrate is not desirable for this could generate additional colored dye after the competing substrate is exhausted. The reverse condition will advantageously extend the colorimetrical range of color response.

Of course what has been said above applies likewise for the aspect of the invention where rather than developing a colorimetrically measurable color there is decreased the amount of color from an intense to a color within a colorimetrically determinable range.

In the aspect in the embodiment of the invention where the competing substrate is irreversibly reduced prior to the chromogen reduction, the relative molar proportion of the two substrates are in the same proportions as explained above. It is important however, that if one wishes to generate color, that there be enough NAD(P)H present to provide for the catalytic oxidization of the competing substrate first to be completed and then allowed for the reduction of the chromogen to generate the color.

It has been discovered in accordance with the invention, that lipoic acid and derivatives (as defined hereafter) are suitable competing substrates. This, however, came surprisingly after a number of failures. Initially this concept was rejected for several reasons. In order to pass test one, as described above, the reaction between NAD(P)H and the competing substrate must be functionally irreversible. This is because the reaction between the NAD(P)H and the chromogen is functionally irreversible. Therefore, if a reversible reaction with the competing substrate were to occur, this reaction would freely reverse, and the regenerated NAD(P)H resulting from this reaction will again react and partition itself between the competing substrate and the chromogen. This process of reaction and partitioning will continue until either the available pool of chromogen is exhausted, or until all of the NAD(P)H is used up to produce dye to cause one equivalent of dye per equivalent of NAD(P)H initially present.

It is well known that the reaction between NAD(P)H and lipoic acid or the derivatives described above (hereafter called lipoic acid compounds) is freely reversible in nature. Indeed, the reaction that occurs in the course of cellular life is the reverse of the desired reaction. Lipoic acid is normally utilized in the production of NAD(P)H, not as an irreversible trap for this molecule. The reversibility of the lipoic acid/NAD(P)H reaction has been well documented in the literature and the equilibrium constant for this reaction measured. This equilibrium constant again argued against the success of using lipoic acid (or the derivatives). Indeed, there is at least one report of an assay for the production of NADH from NAD and reduced lipoic acid amide, DL-dihydrolipoamide (D. J. McKay, and K. J. Stevenson, Biochemistry 18, 4702–4707 [1979]), clearly indicating the reversible nature of this reaction.

When 75 mM lipoic acid was used in the above test system as the soluble, tetramethylammonium salt, the solutions failed the first test outlined above. Surprisingly, when a super-saturated solution of lipoic acid was tested, it passed all three tests. This favorable result was obtained when lipoic acid was incorporated as either the free acid or salt or as a derivative thereof.

No clear explanation is available as of now for this completely surprising and unprecedented result. With hindsight, it was hypothesized that reduced lipoic acid is less soluble than is oxidized lipoic acid. In a supersaturated solution, the reduced lipoic acid is removed from the solution by precipitation, whereby it is not available to react with the enzyme in the reverse reaction. Other explanations are possible and may be a cause of this success in this invention.

These results were also obtained when a solubilizing wetting agent was used in the above experiment. After obtaining this unexpected result, the addition of other ingredients to this reaction mixture was considered to determine whether and how the lipoic acid reaction (or that of the competing substrate generally) could be made to be irreversible.

The use of reagents to make the lipoic acid/NAD(P)H reaction (or the reaction of the equivalent reactants) irreversible has not been discussed in either the patent or the scientific literature so that these studies too were carried out without any suggestion from the prior art.

In this manner, it was discovered that the presence of zinc ions would allow even a saturated, in contrast to supersaturated, solution of lipoic acid (or its equivalents) to pass the above tests. Other reagents that enable lipoic acid to pass these rigorous screening tests are iodoacetic acid, and oxidized 2-mercaptoethanol ethanol, for instance produced by bubbling oxygen gas through a solution of 2-mercaptoethanol.

From these successes, it was reasoned that in accordance with the invention the added reagents must either: (i) chelate (bind to) reduced lipoic acid (herein called dihydrolipoic acid which is intended to include all of the reduced lipoic acid derivatives discussed herein) with a greater affinity than they chelate oxidized lipoic acid; or (ii) react with dihydrolipoic acid, but not, or to a lesser extent, react with lipoic acid.

Several reagents selected using these criteria have been successfully tested, including: metal ions like ferric ion, mercury ion, chromium ion, chloroacetone, dichloroacetone, methyl iodide, and all disulfide compounds currently attempted. All compounds, in addition of those specifically disclosed that will allow lipoic acid in solution to pass the above three tests, are specifically operative and intended to be covered by this invention. In addition, all compounds other than lipoic acid, used either singly or in conjunction with other compounds, that in the presence of a suitable chromogen, pass the three tests disclosed above are intended to be covered by the invention and their absence from being explicitly named from this specification in no way is intended to exclude these compounds or combinations of compounds.

In accordance with the invention, there is used a mixture of a competing substrate and a prodye or chromogen, often a tetrazolium salt to reduce and control the amount of color that is generated in the presence of NAD(P)H. In most cases, the NAD(P)H is produced by the action of a specific dehydrogenase on its substrate. It was found, in this invention, that the amount of color generated plotted against substrate concentration gives a straight and reproducible line. Thus, the concentration of an unknown amount of substrate is determined by comparison of color formed by the unknown sample and a linear standard curve produced by known samples. This color control system can be present in aqueous solution or suspension, or it can be incorporated into a diagnostic device in a dry format, particularly a dry film format as will be further discussed herein. In addition, the diagnostic device comprises a dry film, a dehydrogenase and if necessary, a trap for the oxidized substrate, customary necessary buffer salts, and NAD(P)H.

One skilled in the art is quite capable to identify additional substances which are suitable second substrate since the parameter or tests for such substrate are disclosed herein.

The lipoic acid compounds which can be used in the invention as the competing substrate are those which are reduced in the presence of diaphorase and NAD(P)H and include for example the following: the esters, such as alkyl, e.g., lower alkyl esters (from 1 to 6 carbon atoms), aryl esters, (including alkaryl esters), e.g., having 6-10 carbon atoms including benzyl and phenyl esters, amides like dihydrolipoamide or lipoic acid wherein the carboxy group has been replaced by a sulfonamide group. Also useful derivatives of lipoic acid are those which have substituents on the carbon atoms of the heterocyclic ring and/or on the —($CH_2$)$_4$—COOH chain, including the lengthening of the alkylene group to 6 or more carbon atoms, (or shortening it) or having another atom instead of the sulfur atoms in the ring. Illustrative substituents include keto, hydroxyl, alkyl (e.g., lower alkyl), fluoro, etc. Illustrative compounds are the following: the amide of 4-oxalipoic acid, 4-methyllipoic acid, 5-ketolypoic acid, lipoyl pyridoxamine, 2-fluorolipoic acid, 7,7-difluorolipoic acid, 8-methyl-7-fluorolipoic acid, 8-methyl-7,7-difluorolipoic acid, 8-methyl-7-fluorolipoic acid and 8-methyl-7,7-difluorolipoic acid. Other lipoic acid derivatives are known and such are disclosed in Biochemistry and Chemistry of Lipoic Acids, Schmidt et al in Advances in Enzymology, 32, 423-469 (1969), which is incorporated herein by reference. Specifically included are those derivatives in which the lipoic acid is bonded to amino acid through an amide bond. The synthesis of many substituted lipoic acid analogs which are suitable for this invention, are disclosed in the 1973 Ph.D. Thesis by Hanan N. Alkaysi, University of Kansas, and available from University Microfilms International, Ann Arbor, Mich.

In accordance with the invention, the competing substrate may be reduced completely before a visible color will be generated from the chromogen. This aspect of the invention contrasts with that described above where the color is generated gradually from the chromogen as the second substrate is reduced. In this aspect herein called "threshold gating control", when the amount of color generated by the chromogen is plotted according to the second test described herein all color found is plotted against the NAD(P)H present or found in the reaction, it shows a generated linear relationship after a delay which corresponds to the time or amount necessary for the competing substrate to be reduced, during which delay no visible color is generated. During that period, essentially no chromogen is reduced, at least not enough to generate a visible color change. In that embodiment of the invention, the affinity of the enzyme for the substrate is greater for the competing substrate so that no reduction of the chromogen takes place until all, or virtually all, of the competing substrate is exhausted. Under certain circumstances, the color development will start even though there may still be an amount of about 2 mM of competing substrate present.

Numerous other diaphorase competing substrates in addition to those described above are known as disclosed for instance in Chromogenic Substrates and Dyes and Dye Intermediates in Sigma Chemical Company's catalogue. As described above, for one embodiment of the invention, the competing substrate is reduced currently (at least for a portion of the time, preferably for the major portion of the time), while the chromogen is being reduced and generates color. In this embodiment of the invention, the competing substrate may be considered as providing "random access" with the chromogen to the diaphorase.

For the second major embodiment of the invention, the competing substrate is a preferred substrate for the diaphorase with respect to the chromogen. Unlike the first embodiment, no color will be generated unless a predetermined amount—the threshold amount—of the substance to be measured is present. In this situation color is only generated when the NAD(P)H is present in an excess over the amount necessary for the reduction of the competing substrate. This amount is predetermined by determining at what minimum concentration of NAD(P)H a color will be developed from the substrate selected. Thus, this system allows a digital "on-off" reading which determines whether NAD(P)H is present in a concentration greater than the predetermined threshold. The system for determination of the amount of substrate to be tested contains varying concentrations of NAD(P)H up to and in an amount in excess of the minimum amount.

For the first embodiment of the invention, various competing substrates in addition to the lipoic acid compounds described above, can be used. Typical are various benzoquinones, especially the lower alkoxy (e.g., 6-substituted) benzoquinones and/or benzoquinones hydroxy lower alkyl (e.g., methyl) substituted. Benzoquinones, especially the 1,4-benzoquinones form a suitable class.

Such benzoquinones are known, see for instance CRC Handbook of Chemistry and Physics 1981-1982 Edition, which is incorporated herein by reference. Such benzoquinones are useful if they pass the three tests described above.

Another suitable class of preferred compounds well suited as competing substrates are substituted pyridones such as 4-pyridone-N-acetic acid salts diiodo-substituted. In general, it has been found that unsaturated molecules that are easily reduced and are anti-aromatic are suitable competing substrates; also certain dithio compounds especially those that contain hydrophobic regions in this molecule are suitable competing substrates. For example, dibenzyl disulfide, dithiodibenzenes, dithiodinitrobenzoic acid and tert-butyldisulfide.

Likewise these compounds are known and are listed in the above referred to Handbook. These compounds too are in accordance with the invention, called to pass the three tests described above.

For the other embodiment of the invention, the "threshold gating control test", various inorganic salts like the alkaline earth metals and alkaline metals of ferricyanides are useful. Also useful are benzoquinones, especially unsubstituted or with aromatic substitution like phenyl and other aromatic compounds like benzoquinhydrone (quinhydrone). Other aromatic compounds which in the presence of a chromogen will react with NAD(P)H preferentially are suitable including those having single or multiple aromatic rings (fused or not) which may have various substituents. These compounds may generate a color when irreversibly reduced into the presence of NAD(P)H. This color generation is allowed in this invention as long as the wave lengths for color generation does not completely overlap the region for chromogen color generation.

The rings of these compounds may be hydrocarbon or heterocylic 5 or 6 membered rings (with one or more heteroatoms) like pyridines, thiophenes, furans or pyrroles; they may also be condensed or polycyclic derivatives like indoles, benzofurans, benzothiophenes, quinolines (isoquinolines), carbazoles, acridines, imidazoles, thiazoles, pyrazines, pyrimidines, purines or pteridines, generally substituted on the ring. The only requirement for these heterocylic ring compounds is that they be substrates for the diaphorase. In general, these ring systems which are anti-aromatic are likely to be substrates. The presence of a hetero atom/hetero atom or heteroatom/carbon bond is not necessary; for example, 7,7,8,8-tetracyanoquinodimethane is a suitable substrate. Other compounds will be apparent to one skilled in the art.

The second embodiment of the invention provides a convenient and rapid test for determining a predetermined concentration of a substrate desired to be measured. The device of the invention can be precalibrated so that if or when the concentration of the substrate reaches the predetermined concentration, the color will be generated; if the substrate present is less than that concentration (or absent), no color will be generated. Such "positive" or "negative" test can be conveniently used, for instance, to determine the concentration of alcohol in saliva, or in blood, or sugar in blood or serum. For instance, when the device is calibrated for 0.12% alcohol the color will develop if the concentration in the sample (e.g. saliva) is 0.12% or higher. It is evident that such device is convenient for a sobriety test.

In accordance with the other embodiment of the invention, the second or competing substrate is a substance which is irreversibly reduced by NAD(P)H in a diaphorase catalyzed reaction which decreases by this reaction the amount of color produced in the system where the competing substrate would not be present in the system from a chromogen in the diaphorase catalyzed reactions. The amount of color produced in the presence of the second substrate is in a ratio less than one molecule of dye per mole of NAD(P)H assayed.

The system of the invention can be a liquid system or in a dry format. In the latter, it may be a diagnostic kit. Such diagnostic kit or device comprises a film which can comprise a multilayer sandwich with one layer containing the color control system, and another layer containing the dehydrogenase and a trap for the reacted substrate. The film or film sandwich is suitable for incorporating into a round or rectangular capillary of controlled volume. In this embodiment, the test fluid is drawn into the controlled volume capillary by capillary action, whereupon, it is acted upon by the dehydrogenase to convert all of the specific test material into NAD(P)H and oxidized substrate. The oxidized substrate can, if desired, be trapped in this layer to ensure that the reaction goes to completion and to remove any inhibitory effects of the oxidized substrate.

The NAD(P)H diffuses to the diaphorase which is located in the same film layer or in another layer of the sandwich. The diaphorase uses the NAD(P)H to reduce the competing substrate, for instance the oxidized lipoic acid (or a lipoic acid derivative) and to reduce a tetrazolium salt or other suitable compound as described herein.

The amount of color generated is dependent upon the preset ratio of chromogen to competing substrate. Thus the amount of color that is generated in the capillary is representative of the amount of test material that was contained in the test sample, and the amount of color generated is within the range of color that can easily be detectable by eye.

In accordance with the invention, the system (and the process) of the invention can be used to assay NADH or NAD(P)H directly. In another embodiment, the invention is useful to assay and determine the amount of NADH or NAD(P)H generated by any chemical (also enzymatic) or electrochemical method. The source of the NAD(P)H is not important to or a limiting aspect of this invention. The scope of this invention extends far beyond the specific examples used for purpose of discussion and illustration in the experimental methods section.

For example any of the following commercially available or to be available dehydrogenases or any other dehydrogenase can be substituted for the dehydrogenase used in each specific example: glucose dehydrogenase, L-glutamic dehydrogenase, glyoxylate reductase, hydroxybutyrate dehydrogenase, polyol dehydrogenase, sorbital dehydrogenase, myo-inositol dehydrogenase, isocitrate dehydrogenase, 2-ketoglutarate dehydrogenase, leucine dehydrogenase, lipoamide dehydrogenase, malic dehydrogenase, malic enzyme, succinate semialdehyde oxldoreductase, 5-10-methylenetetrahydrofolate dehydrogenase, NADH peroxidase, cytochrome C reductase, octopine dehydrogenase, 3-phosphoglycerate dehydrogenase, dihydropteridine reductase, pyruvate dehydrogenase, sacharopine dehydrogenase, uridine-5'-diphos- phate dehydrogenase, xylulose reductase, 6-phosphogluconic dehydrogenase, alanine dehydrogenase, dihydrofolate reductase, glucose-6-phosphate dehydrogenase, hydroxyacyl CoA dehydrogenase, 1 acetate dehydrogenase, glycerophosphate dehydrogenase, glycerol dehydrogenase, glyceraldehyde-3-phosphate dehydrogenase, alcohol dehydrogenase, aldehyde dehydrogenase, alpha-hydroxysteroid dehydrogenase, beta-hydroxysteroid dehydrogenase, ferredoxin oxidoreductase, formaldehyde dehydrogenase, formate dehydrogenase, fructose dehydrogenase, and galactose dehydrogenase and other dehydrogenases which fulfill the equivalent functions.

This invention can also be used with any mixture of enzymes to assay a biological molecule providing one of the resulting products of this mixture or string of enzymes is NADH or NAD(P)H. The use of mixtures of enzymes in the assay of biological molecules or of enzymes is known to those skilled in the art. An example of the use of a mixture of enzymes that will result in the production of NAD(P)H in the measurement of glucose is hexokinase and glucose 6-phosphate dehydrogenase. In this system, hexokinase converts glucose into glucose-6-phosphate in the presence of ATP. The glucose-6-phosphate so generated is oxidized by glucose-6-phosphate dehydrogense with the resulting production of NAD(P)H. There is a potentially unlimited number of different combination of enzymes that can be put together by one skilled in the art so that a resulting product is either NADH or NAD(P)H. A list of such enzymes would be obvious to those skilled in the art of enzyme assays. This invention can be used with all such methods using a series of enzyme reaction which have as a product a NADH or NAD(P)H.

It is what occurs thereafter in the color generating aspect of the invention where the inventive embodiments are brought best.

It is specifically noteworthy that this invention is also useful in the determination of the activity of any enzyme, or combination of enzymes, that result in the production of NAD(P)H. For example, the amount of the medically useful enzyme, lactate dehydrogenase can be determined by the rate at which color is produced in a system containing lactate, necessary buffer salts, the ingredient of the invention and an unknown amount of lactate dehydrogenase enzyme. The reduction in the amount of color that is generated in this mixture, as opposed to that generated by conventional mixtures, wherein one molecule of dye is produced per molecule of NAD(P)H produced, will result in an advantageous greater period of time when the color is in the linear, visible discernible range. An example of a combination of enzymes that can be advantageously assayed by use of this invention is amylase in the presence of maltose dehydrogenase, as is described in U.S. Pat. No. 4,427,771 cited above.

The assay system of the invention is provided in a variety of physical embodiments, including test kits and strips. Typically a test kit will include all the reagents described above and the sample is added to the reagents, which may be in a liquid system or a physical (solid) system like filter paper, etc. The competing substrate may be added to the system together with the test substance.

Typically, a test strip will be prepared by impregnating an absorbent material with solutions containing the reagents necessary for the corresponding determination. Suitable absorbent carriers for the test strips of the invention include all those inert absorbent carriers customarily in use for such tests. Most widespread is the utilization of filter paper, but other absorbent cellulose or synthetic resin products can likewise be employed.

Typically, test vials, as is known can be used.

A more detailed description of the figures follows.

FIG. 1 shows the different color intensities generated by potassium ferricyanide in different concentrations in a reaction with diaphorase. Like other compounds disclosed in the specification, potassium ferricyanide is not a "random access" substrate for diaphorase but one that is reacted preferentially over the chromogen.

FIG. 2 shows a similar behavior for benzoquinone.

Figure 3:
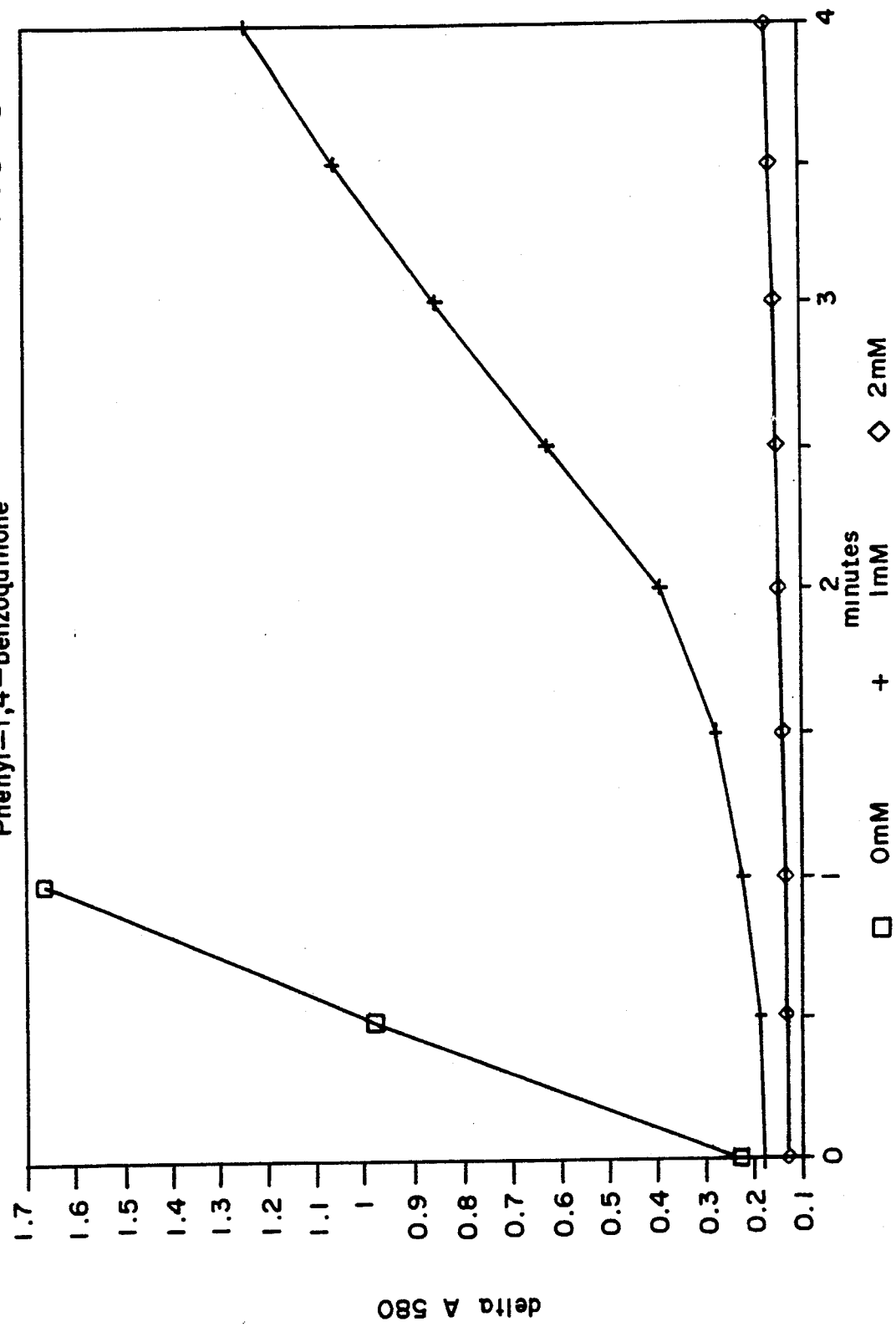
FIG. 3 is a graph which shows the color generated in the diaphorase competing substrate test by phenyl-1,4-benzo-quinone at different concentrations during the time shown.

FIG. 3 likewise shows the color generated by the reaction of phenyl-1,4 benzoquinone by diaphorase at different concentrations of the benzoquinone.

Figure 4:
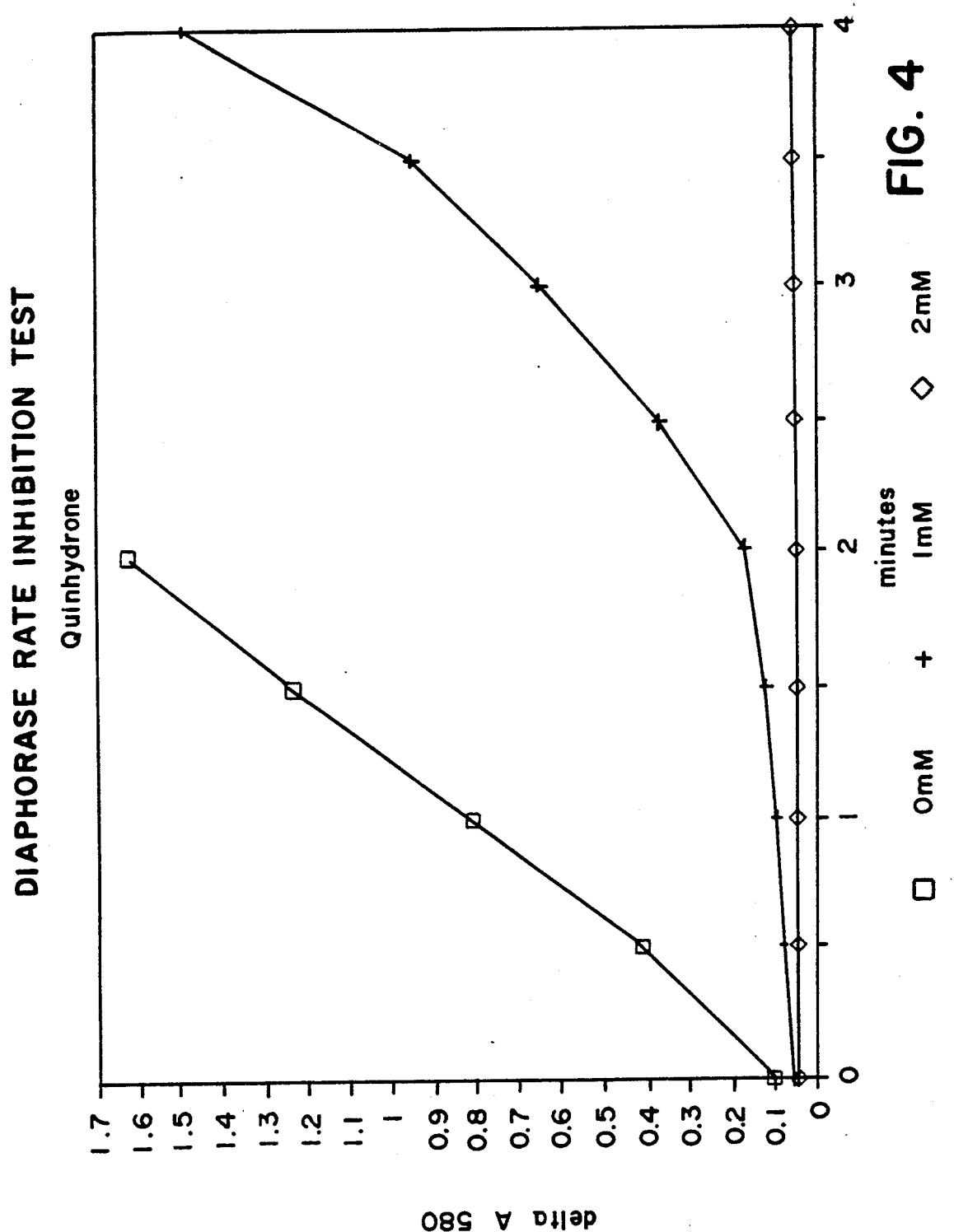
FIG. 4 is a graph which shows the rate of color generated in the diaphorase competing substrate test by quinhydrone at different concentrations during the time shown.

FIG. 4 shows a similar behavior by quinhydrone.

In FIGS. 1 through 4 the respective substrates are preferentially reacted with respect to the MTT chromogen also present in the system.

Figure 5:
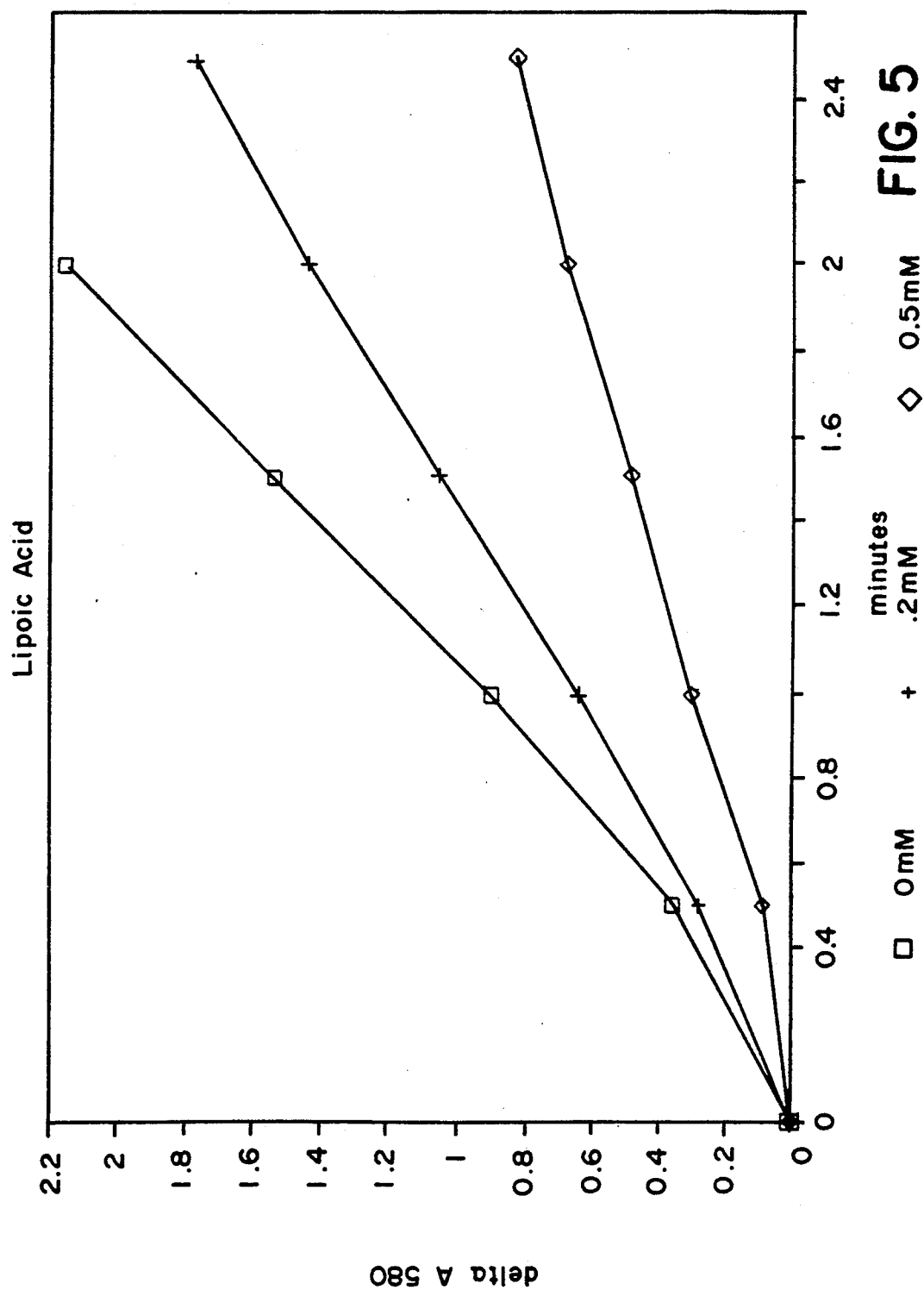
FIG. 5 is a graph which shows the rate of color generated in the diaphorase competing test by lipoic acid at different concentrations during the time shown.

FIG. 5 shows the color produced in the reaction medium which contained 100 mM of potassium phosphate (pH 6.5) buffer, 1 mM MTT chromogen, 0.5 mM NADH, pig heart diaphorase, and a specific amount of lipoic acid as shown. The inhibition of the reaction by lipoic acid at different concentrations is clearly evident.

Figure 6:
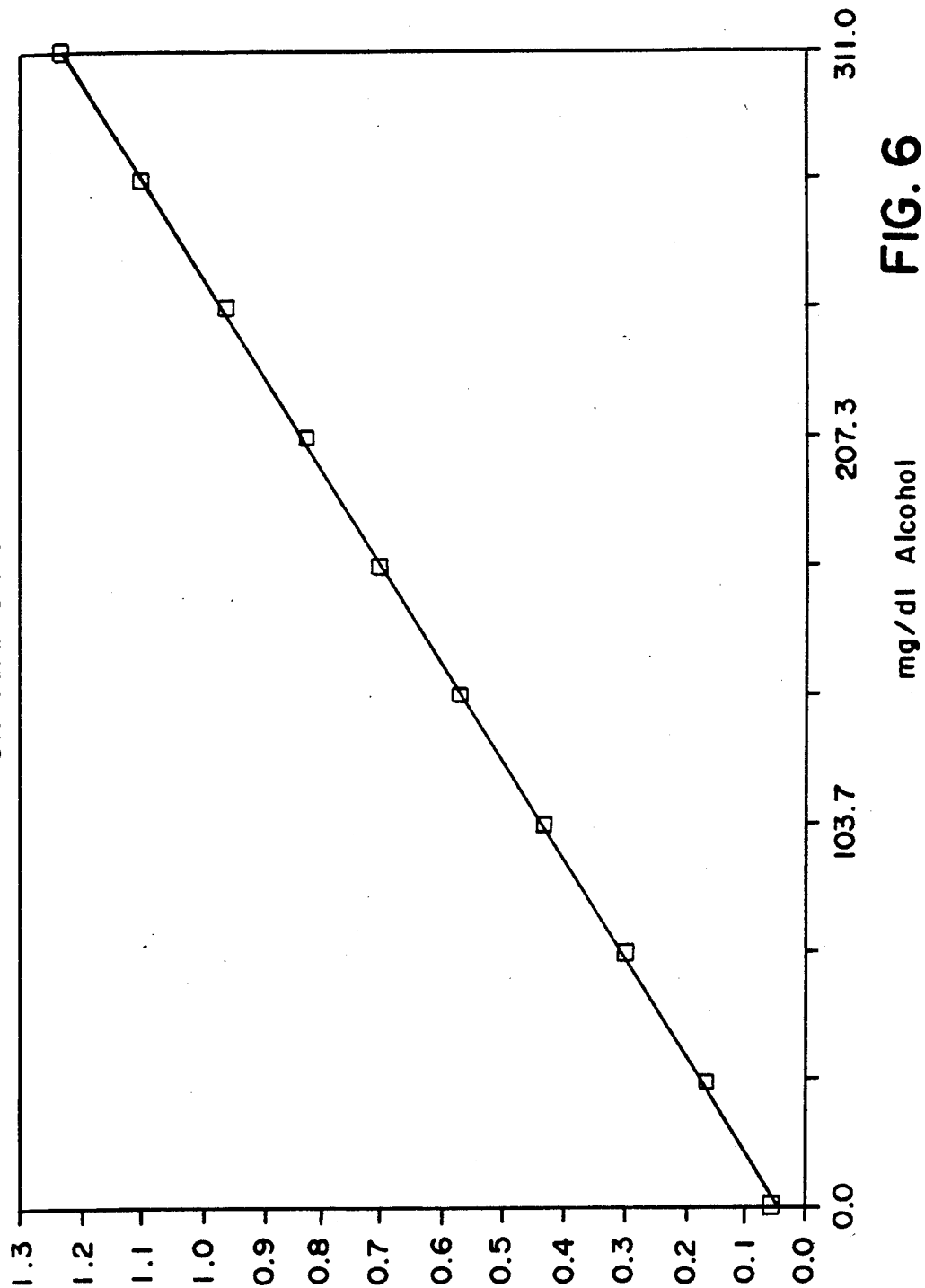
FIG. 6 is a graph which shows an assay of alcohol in a saliva sample using lipoic acid during the time shown.

FIG. 6 is an illustration of the use of the invention for the determination of the amount of alcohol in saliva. Saliva samples are assayed in a solution containing 400 mM of lipoic acid, 5 mM of INT, 200 mM of potassium phosphate, 100 mM of semicarbazide, 400 IU/ml of alcohol dehydrogenase and 150 IU/ml of diaphorase from microorganisms (commercially available from Toyo-Joyo [Japan] or Boehringer Mannheim (Indianapolis, Ind.); the final pH is 6.4.

A sample of saliva containing an unknown amount of alcohol is assayed and the content of alcohol determined by comparison with the standard curve as shown in FIG. 6.

Likewise another biological sample such as serum, containing alcohol in an unknown amount is assayed and compared to the standard curve.

Figure 7:
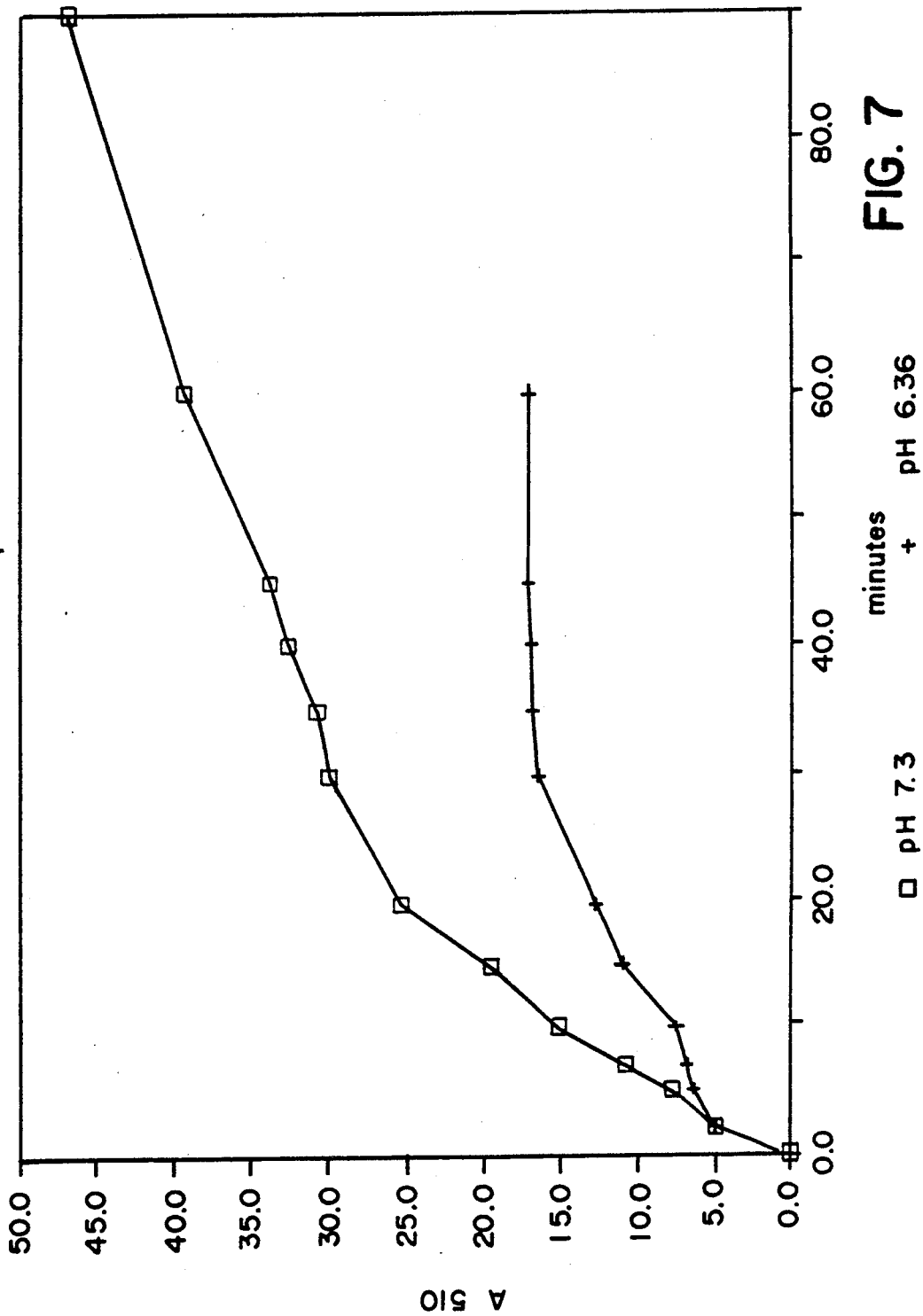
FIG. 7 is a graph which shows how the reaction with lipoic acid is made irreversible (here stopped) by control of the pH, i.e., lowering the pH to 6.3.

FIG. 7 is an illustration of a method for making the reaction of the secondary substrate irreversible, in this case that of lipoic acid. In FIG. 7 the reaction is stopped by lowering the pH in the presence of high concentrations of lipoic acid.

In FIG. 7 the reaction mixture contains 75 mM of lipoic acid, phosphate buffer, 5 mM INT, diaphorase, 40 mM NADH. At a pH of 6.36, the color development comes to a complete stop. At a pH of 7.3, the reaction of the lipoic acid is reversible and continues.

Therefore, in accordance with the invention, a practical method for making the reaction irreversible is to lower the pH to a pH at which the reaction would not proceed any further. Such pH threshold will be a pH lower than approximately 7.0.

Figure 8:
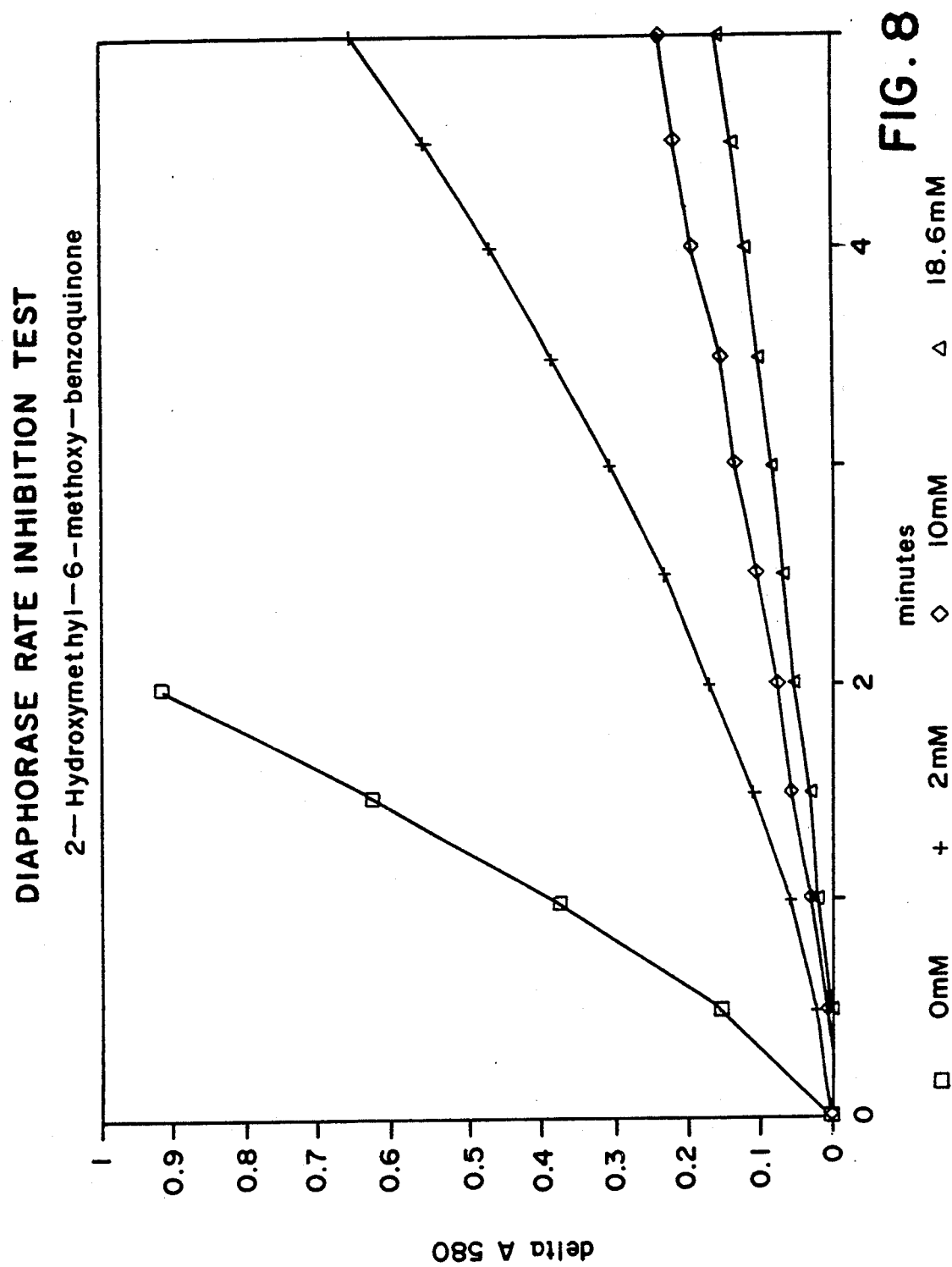
FIG. 8 is a graph which shows an assay corresponding to that shown in FIG. 5 using 2-hydroxymethyl-6-methoxy-1,4-benzoquinone (HMMBQ), rather than lipoic acid.

FIG. 8 is another illustration of the color development of a compound of the invention, showing color development in the presence of a chromogen, in this case MTT. Also shown is the use of a competing substrate 2-hydromethyl-6-methoxy benzoquinone. This competing substrate inhibits the reaction in the same manner as the lipoic acid.

Figure 9:
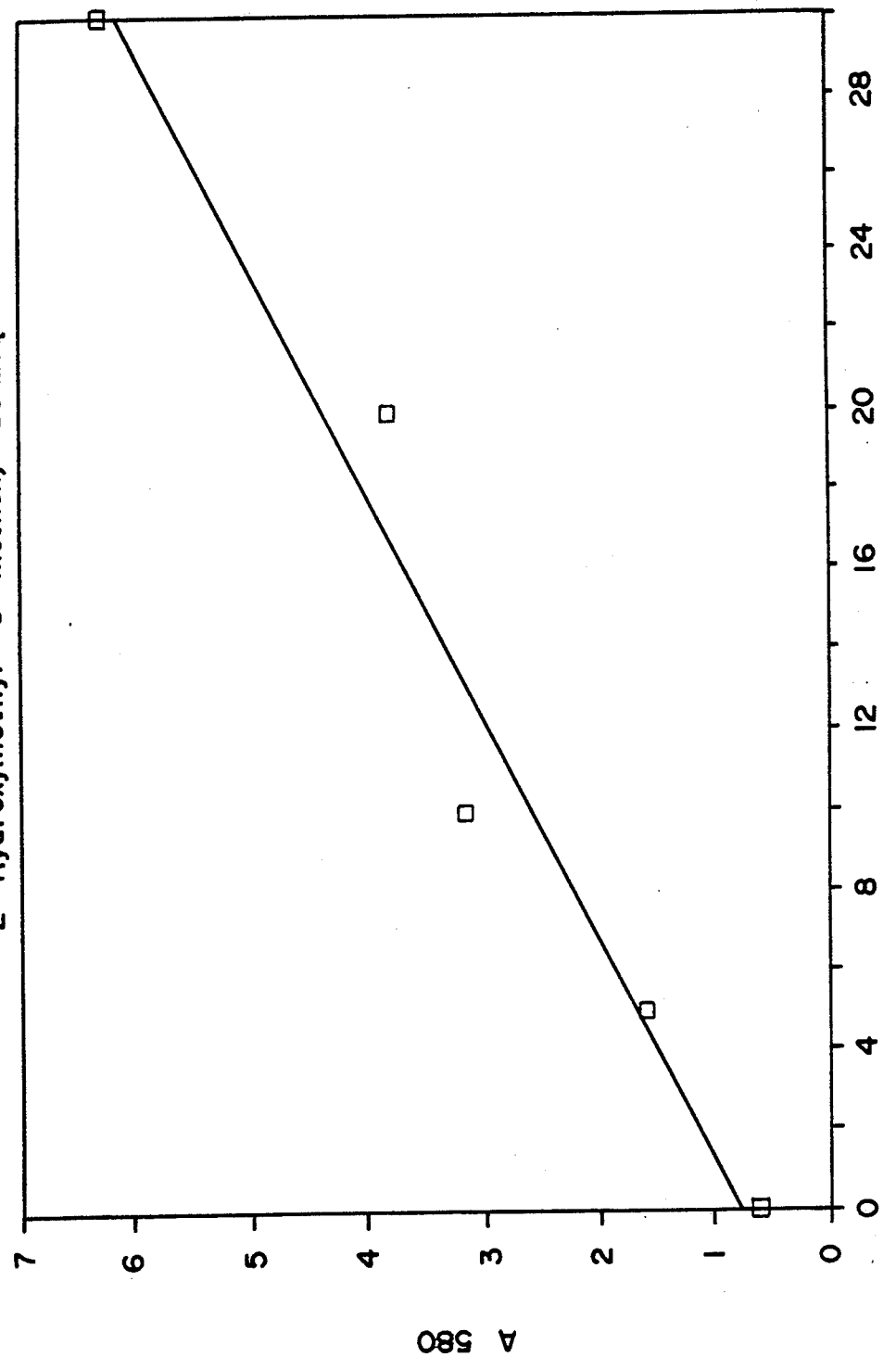
FIG. 9 is a graph which shows the linear color inhibition caused by HMMBQ on the color generated by MTT chromogen.

FIG. 9 is another illustration of the color that was produced in the presence of 4 mM of MTT, 100 mM HMMBQ in a mixture in a reaction system containing pig heart, diaphorase and a pH 7 phosphate buffer. It is noteworthy that the color generated at 40 mM of NADH in this system has an absorbence of 6 at 580 nm. In the absence of HMMBQ, the color that would be generated would be 960. Indeed a 960 reading would not be obtainable as the solubility of MTT is only 20 mM, so that 40 mM of NADH cannot be colorimetrically measured using existing technology.

Another illustration of a compound suitable for use in the invention is diiodo-4-pyridone-N-acetic acid (DIPAA), commercially available from Aldrich Chemical Company, St. Louis, Mo. In a system containing the following: 100 mM of DIPAA, 4 mM MTT (pH 7.4 phosphate buffer), pig heart, diaphorase and this mixture is reacted with 10 mM of NADH, the color of 62 absorbence units at 580 nm is obtained. In the absence of this DIPAA, the color would have been 240 absorbence units, therefore 3.9 times more than was observed.

Figure 10:
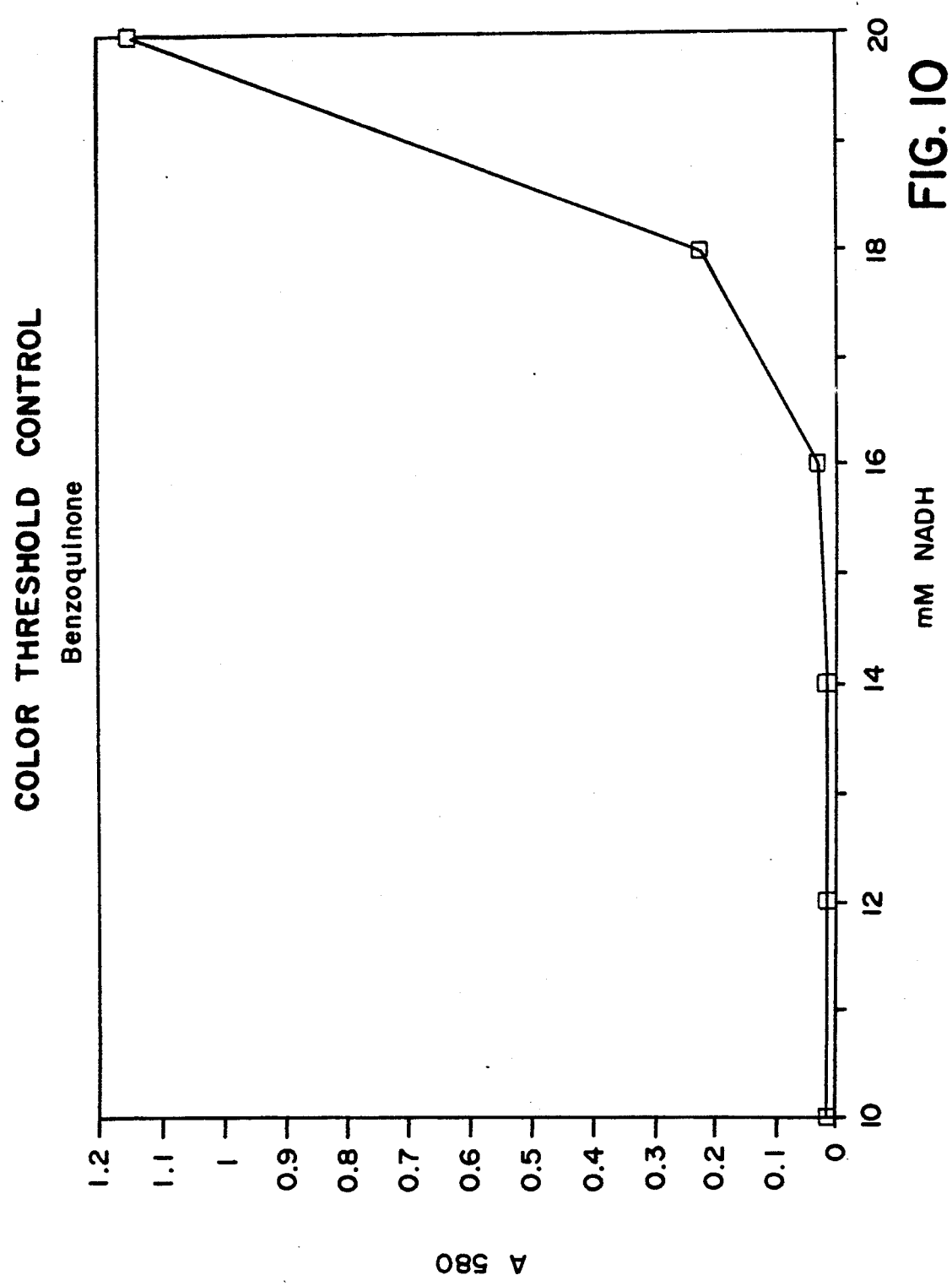
FIG. 10 is a graph which shows the color generated in the presence of 18 mm of benzoquinone and 1 mm of MTT.

FIG. 10 is an illustration of a color-generating system containing 200 mM phosphate buffer (pH 7.3), microorganism diaphorase, 18 mM of benzoquinone and 1 mM of MTT. Concentrations of NADH from 2 mM to 20 mM are added to this reaction. As shown in the figure, no color is generated as long as the concentrations of the NADH is less than 18 mM. When the concentration is greater than this pre-set threshold, the system turns to a very dark blue color. This embodiment of the invention comprises a second substrate (other than the chromogen) which is a preferential substrate for the diaphorase. In such a system the concentration of any given compound is determined at the pre-set threshold. When the color is below that pre-set threshold no color is generated. When the concentration of the test material is greater than the pre-set threshold then a color is generated. The threshold can be pre-set at any desired level. As shown in FIG. 10, the threshold is sharp and clear.

This system (referred to above as "Color Threshold Control System") is very useful for monitoring concentrations of a substance in a solution. An illustration of this embodiment is a measuring device that is colorless in the presence of saliva alcohol less than the legal limit of 0.1% (i.e. 22 mM) and which develops color in the presence of saliva alcohol above that threshold level.

In a practical application of this embodiment, a device has all the necessary ingredients incorporated in a film which is placed over a blue printed sign such as "OK". At all concentrations of saliva alcohol measured which are less than 0.1%, the system remains pale yellow and the "OK" sign remains clearly visible. At concentrations of saliva alcohol above the cut-off of 0.1%, the system becomes dark blue and the "OK" sign would no longer be visible, thus alerting the person that saliva alcohol greater than the legal limit is present.

Figure 11:
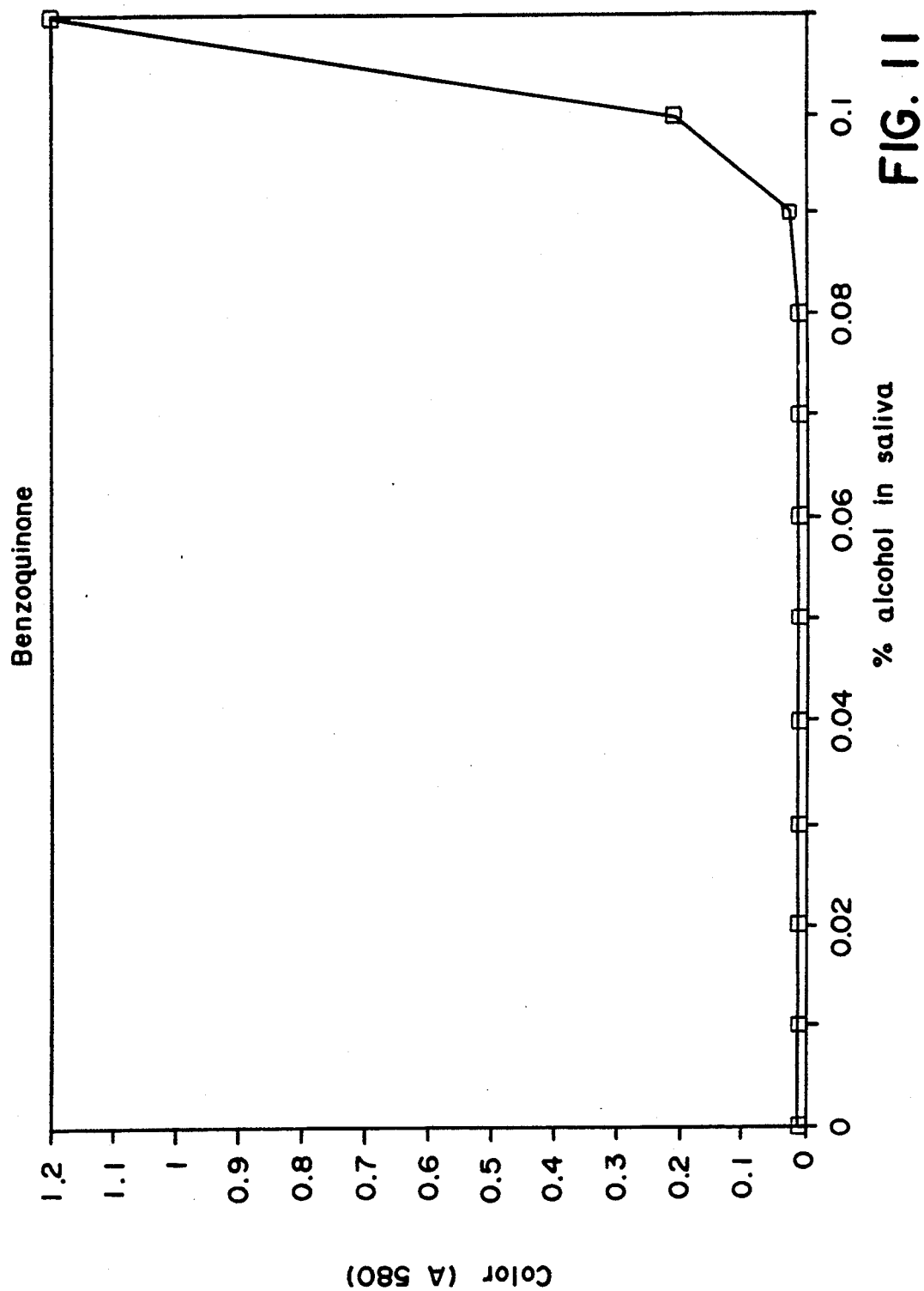
FIG. 11 is a graph which shows the concentration of alcohol in saliva using benzoquinone as the substrate and the threshold concentration of alcohol of 0.1%.

FIG. 11 is an illustration of measurements made in a kit which includes a clear gelatin-based film dried from a solution containing 21 mM benzoquinone, 1 mM MTT, 2 mM NAD, 15 mg/ml BSA, 100-1,000 IU/ml of alcohol dehydrogenase, 50-500 IU/ml diaphorase, 100 mM pH 7.7 tris-buffer, and 20 mM 1,4-diaminobenzene.

The film is positioned in a controlled volume capillary which will contain 10 ul of fluid.

A person's saliva is tested by introducing it into the capillary, the reaction color remains faint yellow until a concentration of 0.1% alcohol or greater is reached; the film then turns dark blue.

Of course, a threshold different from 0.1% of the sample (here alcohol) can be determined.

Figure 12:
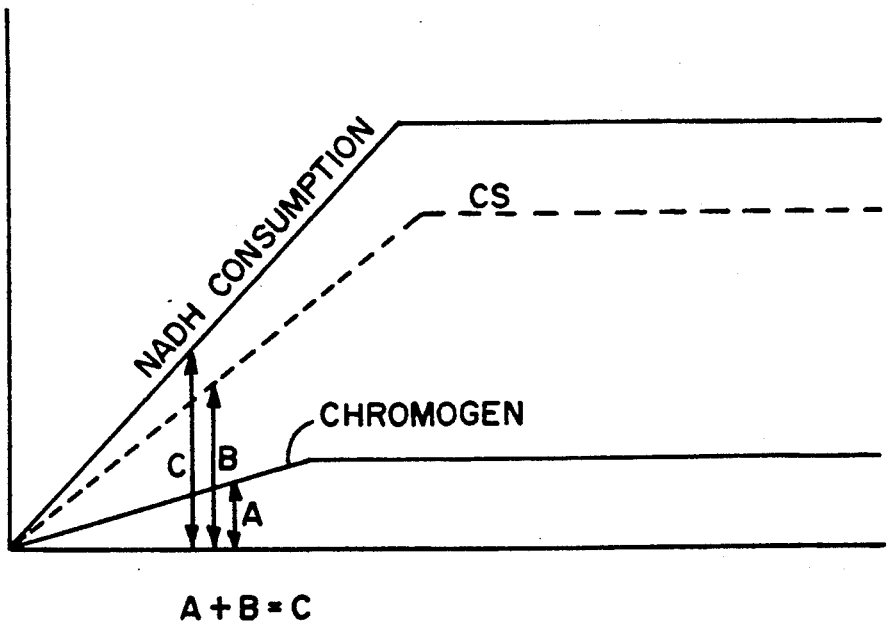
FIG. 12 is a graph which shows the color development due to the chromogen, the presence of a competing substrate, benzoquinone as NADH is being oxidized.

FIG. 12 is a graphic representation of the color generated and linearly related to NADH over a range from 7 mM of NADH to a point where either the chromogen or the competing substrate is exhausted.

Figure 13:
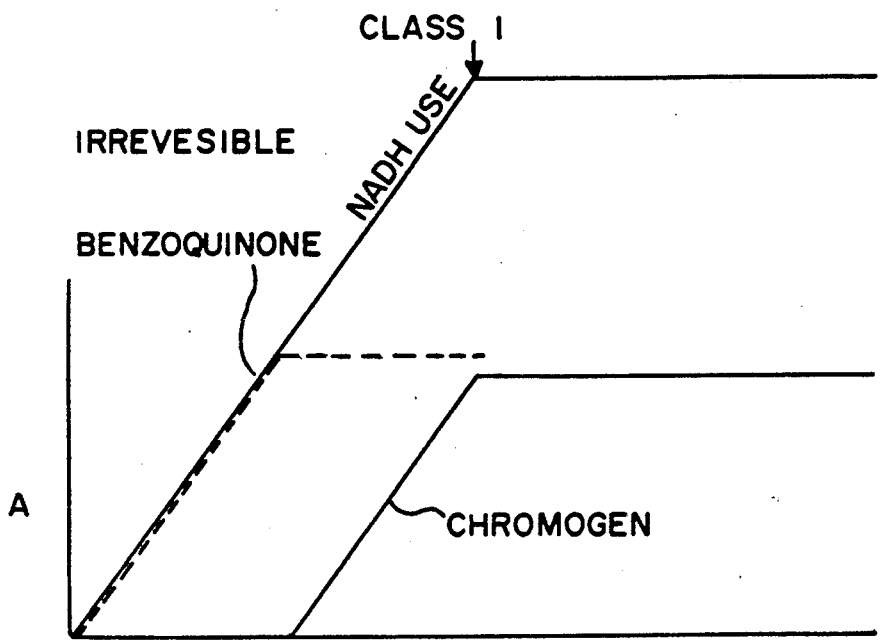
FIG. 13 is a graph which shows the linear relationship of color between the substrate concentration and the competing substrate.

FIG. 13 is an illustration of the reaction of benzoquinone in presence of NADH showing the development of color due to the reaction of benzoquinone before that developed by the chromogen.

Figure 14:
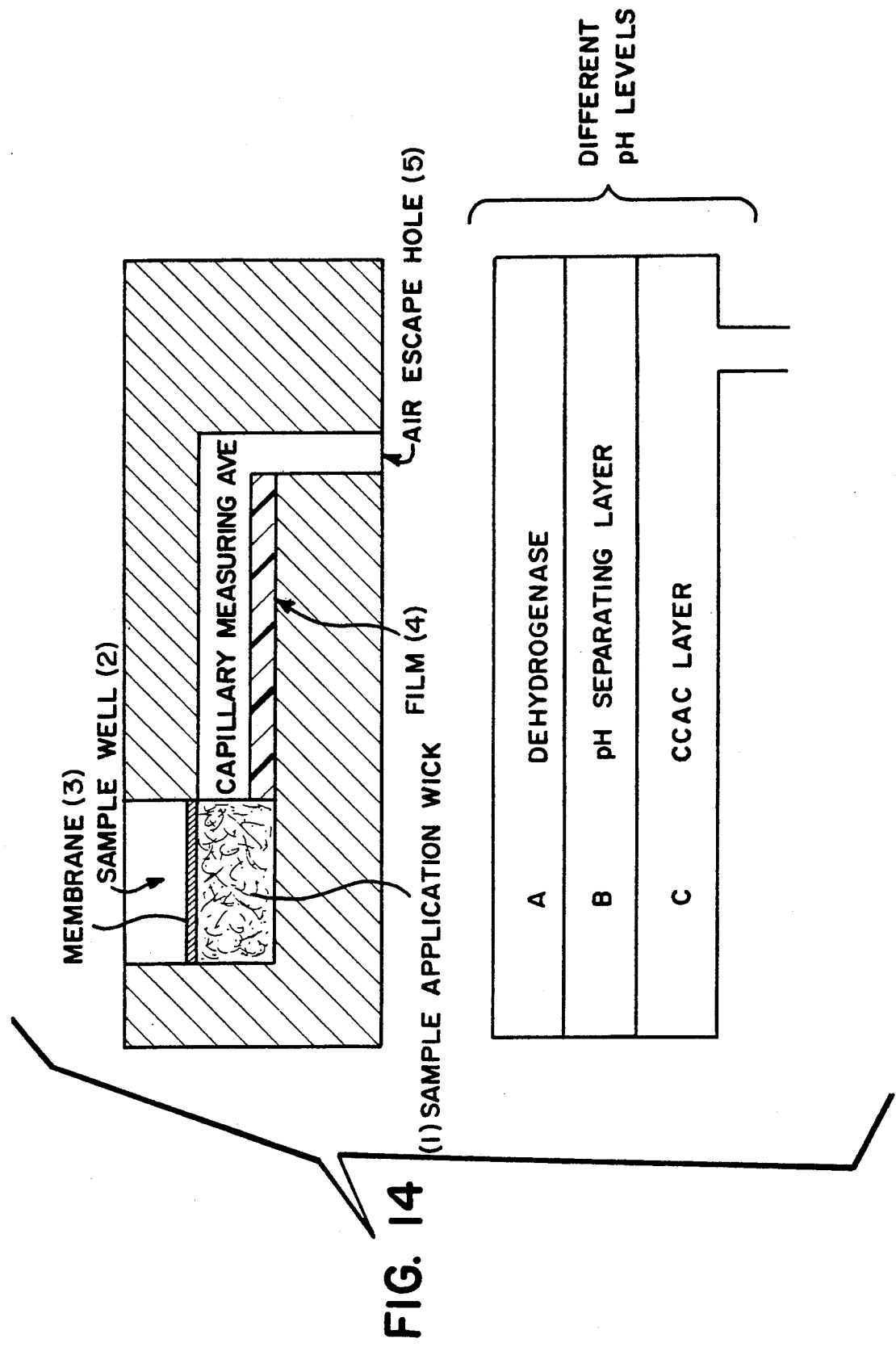
FIG. 14 is a diagramatic representation of a kit embodying the invention.

FIG. 14 is a diagrammatic representation of a physical embodiment of a test kit of the invention wherein 1 shows a wick where the sample is supplied, 2 shows a well for the sample separated by membrane 3 which will prevent passage of cells or other components into the reaction zone, the sample is reacted on the film 4 which is constituted by a layer A impregnated with dehydrogenase, and a layer C impregnated with the constituents of the Chemical Color Amplitude Control (CCAC) system, separated by a layer B to separate the layers A and C which may be at different pHs for optimizing the activity of the exertive enzyme system. An air escape hole 5 is provided to allow for the venting of any gaseous products that may be generated.

Although the present invention has been described and illustrated in connection with preferred embodiments, it is to be understood that modifications and variations may be resorted to without departing from the spirit of the invention, as those skilled in the art will readily understand. Such modifications are considered to be within the purview and scope of the present invention as defined by the appended claims.

The invention having been described adequately to one skilled in the art to make use of it to the extent desired, the following examples are merely illustrative of the invention, and in no way are to be construed as limiting the invention. It is evident that without undue experimentation, one skilled in this art can make many substitutions or variations and still be within the scope of the invention.

The tetrazolium salts used herein are known. Examples of tetrazolium salts are 3,3'-(3,3'-dimethoxy-4,4'-diphenylene) bis[2-(p-nitrophenyl)-5-phenyl-tetrazoliumchloride](NTB), 2-)p-nitrophenyl)-3-(p-iodophenyl)-5-phenyltetrazolium-chloride (INT) or 2-(4,5-dimethyl-2'-thiazolyl)-3,5-diphenyltetrazoliumbromide(4,5-MTT). The concentration of the tetrazolium salt is rather limited by the solubilities of tetrazolium alts and the ultimately formed formazan and generally is 3-100 mg/ml of the reagent. A typical dye which turns colorless is DCIP.

Dehydrogenases are well known and available commercially. Typical substrates which, in accordance with the invention can be measured are, but not limited to, various alcohols like methanol, ethanol, idiotol, sorbitol, inositol; organic acids, like malic acid; aldehydes like formaldehyde, acetylaldehyde; sugars and carbohydrates like glucose, galactose and a variety of other organic compounds which are reactive to enzyme-catalyzed dehydrogenation or hydrogenation, like ketones, aminos (like amino acids), glycerol-3-phosphate, glycine, lactate, maleate and the like.

In accordance with the invention as was discussed above, the affinity of the enzyme(s) for the respective substrates is a guide for the selection of the substrates and accordingly which embodiment of the invention is sought to be used. A general method of determining the dissociation constant ("Ks") of a two substrate enzyme is found in Rose I. A., O'Connell E. L. and Letwins J., *Bio. Chem*, 249, pps. 563–568 (1974) which is incorporated herein by reference. For additional information for determining the bonding constant, see Enzyme Kinetics, Plowan, K., McGraw Hill, 1972.

Tetrazolium salts are disclosed in U.S. Pat. No. 4,490,465, column 6; U.S. Pat. No. 4,491,631, column 14; U.S. Pat. No. 4,598,042, column 18; U.S. Pat. No. 4,351,899, column 2; U.S. Pat. No. 4,271,265, column 5; U.S. Pat. No. 4,247,633, column 3; U.S. Pat. No. 4,223,090, column 3; U.S. Pat. No. 4,215,917, column 3; U.S. Pat. No. 4,142,938, column 3; U.S. Pat. No. 4,024,021, column 3; U.S. Pat. No. 3,867,259, column 2; U.S. Pat. No. 3,867,258, column 5; U.S. Pat. No. 3,791,931, column 1; U.S. Pat. No. 4,254,222, column 5; incorporated herein by reference.

To maintain the pH of the solution at a desired value during the reaction, a conventional buffer solution is used. Examples of the buffer solution are found in U.S. Pat. No. 4,416,983, column 3; U.S. Pat. No. 4,592,996, column 5; U.S. Pat. No. 4,271,265, column 5; U.S. Pat. No. 3,867,259, column 4; U.S. Pat. No. 3,867,258, column 2; U.S. Pat. No. 4,254,722, column 3; incorporated herein by reference.

The invention is useful as described herein for the measurement and determination of the amount of an organic compound generally in a fluid sample, more commonly in a biological fluid sample. Of course, a very large number of such compounds are of interest including: carbohydrates—e.g. glucose, amino acids, proteins, alcohols, sugars, ketones. Illustrative are the following: biological fluids including serum, plasma, whole blood, urine, saliva, amniotic and cerebrospinal fluids, and semen.

The fluids are not limited to those obtained from humans but also include those obtained from other mammals in general, including, for example, bovine, porcine, equine, feline and canine fluids. The fluids also include those obtained from non-mammals such as fish.

EXAMPLE 1

Colorimetric Assay of Alcohol in Liquid Solution 100 ul of saliva is added to 100 ul a solution so that the resulting 200 ul will have a final concentration as follows.

The solution is prepared of the following components. 200 mM lipoic acid is prepared by addition of 4M lipoic acid dissolved in 100% Triton X-100; 2% polyethylene glycol (1,000 molecular weight); 80 mM potassium phosphate monobasic; 120 mM potassium phosphate (dibasic); 100 mM semicarbazide, (from a 800 mM, pH 7.3 stock solution); 100 mM NAD; 2 mM INT; and 3 mg 1 ml BSA.

To the solution there is added: 100 international units (IU) per ml of alcohol dehydrogenase (from yeast, Sigma Chemical Company, St. Louis, Mo.); and 80 IU/ml diaphorase from microorganism (Boehringer Mannheimer Corporation, New York, N.Y.).

The contents of the tubes are mixed and left to react for five minutes. A standard curve is prepared by use with saliva that contains ethanol concentrations between 0 and 75 mM ethanol. After a five minute reaction time, the samples are read either directly in a 0.1 cm path length cuvette, or after a dilution in 50% dimethyl formamide.

Instead of saliva samples, serum samples from an individual can be used.

The absorbence that would have been seen in the absence of the INT at 75 mM ethanol is 675 absorbence units per cm, which is outside of the visible range.

Saliva samples are tested. The concentration of alcohol is determined to be 0.25, 0.1,, 1.50, 7.0, 10.0, 12.0, 23 and 55 mM of ethanol when recorded against the standard curve.

The standard curve obtained from the reaction yields a straight line between 0.1 O.D. units per cm and 24 O.D. units per cm (0 and 1.2 O.D. units per 0.5 mm) at 510 nm, for 0 and 75 mM ethanol, respectively.

The absorbence that would have been seen in the absence of the INT at 75 mM ethanol is 675 absorbence units per cm, which is outside of the visible range.

EXAMPLE 2

Colorimetric Assay of Lactic Acid in Liquid Solution 100 ul of serum or buffer containing lactic acid of between 0 and 25 mM is added to 100 ul of a solution so that the final concentration will be as follows.

A mixture is prepared as follows: 150 mM lipoic acid is added at a pH of 7, tetramethylammonium chloride salt; 1.50 mM INT; 5 mg BSA; 200 mM pH 6.5 MES buffer; 40 mM hydrazine, (from a pH 7 stock); 0.2% Tween 80 (a known wetting agent); 2 mM NAD; 100 IU/ml yeast lactate dehydrogenase (Sigma Chemical Company); and, 60 IU/ml pig liver lipoamide dehydrogenase (Sigma).

The reaction reaches a stable end point within one minute, at which time the color generated is read directly in a spectrophotometer in 1 cm or 0.1 cm path length cuvettes. The color generated by the standard curve yields a straight line between 0.1 and 8 absorbence units per cm at 510 nm. In the absence of INT, the amount of color generated at this wavelength would have been 180 absorbence units per cm.

The lipoic acid is replaced by 60 mM of DL-lipoamide beta-alanine. A like color intensity is obtained which can be read directly.

EXAMPLE 3

Assay of 0–150 mM Sorbitol in Liquid Solution 100 ul of known or unknown sorbitol solutions that have a pH ranging between 4 and 10 are added to 100 ul of a solution, so that the resulting solution has a composition as follows.

400 mM lipoic acid added at the pH of 7, tetramethylammonium chloride salt; 150 mM oxidized 2-mercaptoethanol; 4% Triton X-100; 0.2% Tween 80; 8 mg 1 ml BSA; 200 mM potassium phosphate pH 7.4 buffer; 150 mM semicarbazide; 5 mM NAD; 2 mM INT; 120 IU/ml sorbitol dehydrogenase or 150 IU/ml polyol dehydrogenase (Sigma); 60 IU/ml diaphorase from *Clostridium kluyveri* (Sigma or Genzyme, Boston, Mass.), from a 1,500 IU/ml stock that contained 0.5 mg/ml flavin adenine dinucleotide (FAD); and, 30 mM tris-Cl, pH 7.5 buffer.

The reaction is complete in one minute, at which time the sample is diluted 1/10 in 50% dimethyl formamide and read spectrophotometrically. The standard curve yields a straight line between 0.1 and 32 O.D. units at 510 nm for 0–150 mM of Sozbitol. The absorbence seen at this wavelength in the absence of INT would have been 1,350 absorbence units. In this example, the amount of color that was generated at every concentration of sorbitol was reduced by a factor of 42 and into the visible range, from that would have been seen utilizing pre-existing technology.

EXAMPLE 4

Using the same procedure as shown above, the chromogen is replaced by DCPIP (1 mM) which is a dye which becomes of a less intense color as it is reacted. The reaction medium also includes 100 mM of hydroxymethyl benzoquinone as the competing substrate, 500 mM of phosphate buffer (pH 7.2) and NAD(P)H is measured in concentrations up to 50 mM. The color decrease due to the dye comes within a colorimetrically readable range.

EXAMPLE 5

Assay of Beta-Hydroxy Butyrate (2HB) in Liquid Solution 100 ul of human serum containing a unknown concentration of 2 HB was mixed with 100 ul of a solution so that the final mixture contained: 80 mM DL-lipoic acid, added from a 2M solution in Triton X-100; 150 mM HEPES buffer, pH 7.2; 35 mM divalent metal ion-chloride; 10 mM NAD; 1.0 mM MTT; 15 mM 1-6 hexanedihydrazine; 60 IU/ml beta-hydroxybutyrate dehydrogenase (Sigma); and, 50 IU/ml tortula yeast lipoamine dehydrogenase (Sigma).

A biological sample was determined to contain 45 mM of 2 HB.

A straight curve is also obtained by using concentrations of HB between 0 and 25 mM. The resulting reaction is complete within one minute. The color generated in this reaction reaches a high of 15 absorbence units at 580 nm. In the absence of the lipoic acid, the color generated would have reached 300 absorbence units.

A sample of human serum is determined to contain 15 mM of 2 HB following the above procedure.

EXAMPLE 6

Production of a Dry Film Layer Containing the Chemical Color Amplitude Control System Suitable films for diagnostic tests are prepared by different procedures. Three are illustrated below.

Method 1: To the cavity in a well washed glass or plastic plate containing a cavity that is approximately 0.5 inch in diameter and approximately 0.5 mm deep is added 20 ul of a solution containing the following: 6% gelatin; 1.5% polyethylene glycol of molecular weight equal to or greater than 1,000; 20% sorbitol; 100 mM 1,4-butanedihydrazine; 100 mM MES buffer, pH 6.5; 0.2% Tween 80; 15 mg/ml BSA; 150 mM lipoic acid (as the pH 6.5 tetramethylammonium salt); 1.25 mM INT; and, 100 IU/ml pig heart lipoamide dehydrogenase.

The solution is gently heated to 37° C., and applied to the wells. The wells are then cooled to allow the gelatin to gel. Then the film is air dried by passing a stream of warm air over the film. Alternatively, the film is freeze dried under vacuum. When the films are dry to the touch, they are placed in a chamber and subjected to high vacuum for a period of time between 5 minutes and 30 minutes, sufficient to remove remaining traces of water. The films so generated are stored in the presence of a desiccant at temperatures below 30° C. Under these conditions, the films are stable for months.

These films are treated for operation of the Chemical Color Amplitude Control (CCAC) system by development with solutions containing between 0 and 100 mM of NAD(P)H.

In method (a) the polyethylene glycol is omitted; so is the butanedihydrazine, and the sorbitol (the latter normally added if enzyme stability needs to be increased). Likewise the Tween 80 can be omitted. The films which are obtained are suitable for use in the invention.

Method 2: To a clean test tube is added: 30 ul 0.91M MES buffer, pH 6.7; 12.5 ul 350 mg/ml BSA; 60 ul 10 mM INT; 15 ul 200 mM NAD; 40 ul 3,000 IU/ml diaphorase isolated from microorganisms (Boehringer Mannheim); 22.5 ul 1.0M lipoic acid at pH 6.7 tetramethylammonium salt; and, 72 ul 25% gelatin warmed to 40° C.

The mixture is kept at a temperature sufficiently high so as to prevent gelling, then sprayed onto a sheet of clear plastic to an even 0.1 mm thickness. The sheet is dried in air and cut into even sized squares for later use.

Method 3: To a clean test tube are added: 12.5 ul MES pH 6.5 buffer; 12.5 ul 350 mg/ml BSA; 60 ul INT; 15 ul 200 mM NAD; 20 ul 1,000 IU/ml pig heart lipoamide dehydrogenase; 22.5 ul 1.0M lipoic acid at pH 7, tetramethylammonium salt; 20 ul 80% sorbitol; 58 ul water; 78 ul 25% gelatin; and, 10 ul of either 1.0M zinc sulfate or 1.0M iodoacetic acid.

A continuous strip of plastic film is dipped into this solution, and the film then passed by a drying station which contains a warm air source or a radiant heat source. The film is then rolled onto a spool, and stored in a cool dry place until further use, or used immediately.

A similar strip is prepared using 22.5 ul 1.0M lipoic acid amidated to 2-amino propanoic acid.

EXAMPLE 7

Production of a Multilayer Film for the Colorimetric Determination of Alcohol A film for use in the invention, prepared by one of the methods detailed above, is used as the starting point in this production. The film is then covered with a very thin layer of gelatin (1 ul, applied by spraying) which contains: 6% gelatin; 0.1% Triton X-100; and 30 mM pH 7.4 buffer.

This thin film is allowed to gel, then the well is covered with another layer containing: 140 mM potassium phosphate; 80 mM semicarbazide; 10 mM NAD; 15 mg/ml BSA; 0.5% Tween 80; 40% sorbitol; 6% gelatin; and 100 IU/ml alcohol dehydrogenase.

The sandwich so formed is cooled so that all layers will gel. The sandwich is then frozen and treated with high vacuum to remove moisture. This stable sandwich will reconstitute to generate a gel that turns color in the presence of aqueous ethanol or methanol. The color generated by the presence of each of these alcohols is compared to a chart (color calibrated). The intensity of the color corresponds to the concentration of the ethanol.

A number of blood samples are taken from patients and determined to contain varying concentrations of alcohol.

Concentrations are determined by comparison with a standard color scale.

EXAMPLE 8

Filter Paper Impregnated with the Chemical Color Control System and Alcohol Dehydrogenase for Production of an Alcohol Saliva Diagnostic A solution is prepared that contains: 200 mm potassium phosphate, pH 6.6; 120 mM semicarbazide, pH 6.6; 1 mM NAD, 15 mg/ml BSA; 4 mM INT, 120 mM lipoic acid, 4.5% sorbitol; 200 IU/ml lipoic acid dehydrogenase for yeast; and 20,000 IU/ml alcohol dehydrogenase.

A cellulose filter paper (for example Whatman #42), on a continuous roll is passed over a series of rollers. One of the rollers is positioned so as to dip the paper into the solution described. Immediately after the paper is dipped, the paper is lead past a drying station where it is well-dried by the action of hot air. The dry paper is then dipped into another solution that contains: gelatin 0–6%, in this sample about 3%; pH 6.6 phosphate buffer 2–200 mM, in this sample about 50 mM; Tween 80 at about 0.1%; polystyrene at about 0.5%, (which has been finely dispersed in the semi-aqueous solution by sonic action); optionally there can be used other suitable agents that will contribute to the stabilization to the enzymes.

The wetted paper is again air dried, and the dried paper is passed over rollers onto a take-up roll. The paper is then processed by feeding to an automated cutter that will section the paper into small uniform sections of approximately 0.24 cm per side. Each section is then welded into a plastic, uniform volume capillary. The necessary wicking material and membranes that will draw sample to the measuring paper and prevent the passage to cells to this measuring paper are included in the final assembly. The final assembly has the components shown in FIG. 14 following drawing.

In the kit described above (FIG. 14), the capillary layer also contains a non-ionic wetting agent to facilitate the spread of the substrate. The dehydrogenase layer A and the CCAC layer can be one single layer. A separation layer B is useful to avoid that resistant(s) from the dehydrogenase reaction other than the desired oxidized substrate and NAD(P)H interfere with the color development test in the CCAC layer and acts thus as a trap (e.g. inhibitors of the diaphorase). Other variants of this construction can of course be considered.

The system of the invention will normally contain as is known various buffers compatible with the enzymes, stabilizers (for the enzymes on the resulting dyes) and, if desired, wetting agents. Illustrations are BSA, polyalcohols, mild reducing agents, non-ionic wetting agents. The pH is generally in the range of about 4 to about 10 (being optimized for the different enzymes used). The optimum pH ranges for different enzymes, or some enzymes of different origins are known. For instance, amongst the dehydrogenases, alcohol dehydrogenase has an optimum pH of 9.0, lactic and dehydrogenanse, an optimum pH of 8.00. Amongst the diaphorase that from pig's heart has an optimum pH of 6.0, that from microorganisms, a pH of 7.3. Thus one skilled in the art will find it advisable to adjust the environment wherein the enzymes is to be active (be it the filter paper strip, the test tube, or other liquid or solid medium, etc.) at the optimum pH or within or close to the optimum range or value.

Also useful in the practice of the invention will be chemicals that form gels or films that permit storing the essential ingredients in a dry state and rehydrating in the presence of an aqueous solution and controlling color generation. For such known chemicals see U.S. Pat. No. 4,556,634, column 4, which passage is incorporated herein by reference.

As is known, reduced or oxidized nicotinamide-adenine dinucleotide is represented by NADH, and NAD+, respectively and nicotinamide-adenine dinucleotide phosphate by NADPH, NADP+. Herein the compounds are generically referred to as NAD(P)+ and NAD(P)H.

The preceding examples can be repeated by substituting or modifying the generically or specifically described reactants and/or operating conditions of this invention for those used in the preceding examples.

The invention has been described in detail with particular reference to certain preferred embodiments thereof, but it will be understood that variations and modifications can be effected within the spirit and scope of the invention.

What is claimed:

1. An assay system for colorimetric measurement and determination of NAD(P)H, NAD(P), or an enzyme substrate which reacts to form or consume NAD(P)H wherein the assay system comprises:
   a diaphorase which catalyzes NAD(P)H-dependent reduction of a chromogen to cause a visible color change,
   a chromogen which is an electron accepting substrate of the diaphorase, and which produces a color change upon reduction by NAD(P)H, and
   a non-chromogenic competing substrate of the diaphorase, in an amount sufficient to increase the range of concentrations that can be measured by the color change of the chromogen when the competing substrate is irreversibly reduced by the diaphorase,
   wherein the change in color caused by reduction of the chromogen occurs in a ratio of less than one molecule of dye for each molecule of NAD(P)H produced and is indicative of the concentration to be determined.

2. The system of claim 1 wherein the color change is an increase in color.

3. The system of claim 1 wherein the diaphorase catalyzes the reduction of the competing substrate and the chromogen with similar efficiency.

4. The system of claim 3 wherein said competing substrate causes the amount of color generated by said chromogen to be linearly related to the concentration of the NAD(P)H.

5. The system of claim 4 wherein a linear relationship occurs over all concentrations measured.

6. The system of claim 1 wherein the chromogen is not reduced until after the non-chromogenic competing substrate is reduced.

7. The system of claim 6 wherein the competing substrate is a benzoquinone.

8. The system of claim 6 wherein sufficient chromogen reduction to generate a visible color change does not occur until virtually all of the competing substrate is reduced.

9. The system of claim 1 which includes means for causing the reduction of the competing substrate to be irreversible.

10. The system of claim 9 wherein the means for causing the reduction to be irreversible is a reactant for the reduced competing substrate.

11. The system of claim 10 wherein the reactant is dihydrolipoic acid present as a supersaturated solution.

12. The system of claim 11 additionally comprising zinc ions.

13. The system of claim 9 wherein the competing substrate is a lipoic acid compound, and the means for causing the reduction to be irreversible is a reactant that reacts preferentially with the reduced lipoic acid compound as compared with the oxidized lipoic acid compound.

14. The system of claim 13 wherein the reactant is selected from the group consisting of iodoacetic acid, oxidized 2-mercaptoethanol, ethanol, chloroacetone, dichloroacetone, methyl iodide, dibenzylsulfide, 2-hydroxy-methyl-6-methoxy-1,4-benzoquinone diiodo-4-pyridone-N-acetic acid, salts of iodoacetic acid, and salts of diiodo-4-pyridone-N-acetic acid.

15. The system of claim 13 wherein the reactant forms a chelate compound with the competing substrate.

16. The system of claim 15 wherein the reactant has a greater affinity for the reduced competing substrate than for the oxidized competing substrate.

17. The system of claim 15 wherein the reactant is a metal ion.

18. The system of claim 17 wherein the metal ion is selected from the group consisting of zinc, mercury, chromium and ferric ions.

19. The system of claim 1 wherein the competing substrate is a lipoic acid compound.

20. The system of claim 19 wherein the lipoic acid compound is selected from the group consisting of DL-alpha-lipoic acid, DL-alpha-lipoamide, DL-lipoyl glycine, DL-dihydrolipoyl glycine, DL-lipoyl beta-alanine, DL-lipoyl glycylglycine, DL-carboethoxy lipoanilide, DL-lipoanilide and DL-dihydrolipoanalide.

21. The system of claim 1 wherein the competing substrate is selected from the group consisting of an antiaromatic compound, a disulfide and a dithiobenzene.

22. The system of claim 1 which also includes an organic analyte oxidizable by NAD(P)-dependent dehydrogenase to yield NAD(P)H, wherein the concentration of NAD(P)H is indicative of the concentration of the organic analyte.

23. The system of claim 22 wherein the analyte is in a biological medium.

24. The system of claim 23 wherein the biological medium is saliva, blood or urine.

25. The system of claim 24 wherein the biological medium is urine containing uric acid, and wherein the concentration of uric acid is to be determined.

26. The system of claim 24 wherein the biological medium is saliva containing alcohol, and wherein the concentration of alcohol is to be determined.

27. The system of claim 24 wherein the biological medium is blood containing cholesterol, and wherein the concentration of cholesterol is to be determined.

28. The system of claim 22 wherein the organic analyte is selected from the group consisting of carbohydrates, polyalcohols and ketones.

29. The system of claim 28 wherein the analyte is selected from the group consisting of alcohol, cholesterol, lactic acid and acetone.

30. The method of claim 22 wherein the diaphorase catalyzes the reduction of the competing substrate and the chromogen with similar efficiency.

31. The system of claim 1 wherein the molar proportion of competing substrate to chromogen is at least 1 to 1.

32. The system of claim 1 wherein the competing substrate is present in excess over the chromogen.

33. The system of claim 1 wherein the chromogen is a tetrazolium salt.

34. The system of claim 33 wherein the tetrazolium salt is selected from the group consisting of NTB, INT, 4,5-MTT and DCIP.

35. The system of claim 1 wherein the competing substrate is selected from the group consisting of semicarbazide, hydrazine, hydroxymethyl benzoquinone, hexane-dihydrazine and 1,4-butane dihydrazine.

36. The system of claim 1 wherein the competing substrate is potassium ferricyanide.

37. A method for colorimetric measurement of the amount of an organic analyte in a sample wherein the method comprises:
(a) oxidizing the organic analyte in the presence of NAD(P) and an NAD(P)-dependent dehydrogenase to produce NAD(P)H in an amount proportional to the amount of organic analyte,
(b) irreversibly reducing a chromogen which is an electron accepting substrate of diaphorase in the presence of diaphorase and the NAD(P)H produced in (a) causing a measurable color change,
(c) and irreversibly reducing a non-chromogenic competing substrate of diaphorase in the presence of diaphorase and the NAD(P)H produced in (a), wherein the competing substrate is present in an amount sufficient to expand the range of concentrations that can be measured by the color change of the chromogen,
(d) wherein the color change produced upon reduction of the chromogen is in a ratio of less than one molecule of dye per molecule of NAD(P)H, and
(e) measuring the color change caused by the chromogen, thereby determining the amount of analyte in the solution.

38. The method of claim 37 wherein the irreversible reduction of the chromogen and the competing substrate is concurrent or substantially concurrent.

39. The method of claim 38 wherein the sample is not diluted prior to adding the sample of the system.

40. The method of claim 38 wherein the concentration of the organic analyte in the sample is at least 0.5 mM.

41. The method of claim 37 wherein the irreversible reductions of the competing substrate and chromogen are sequential, the reduction of the chromogen following that of the competing substrate.

42. The method of claim 41 wherein a visible color change does not take place until virtually all of the competing substrate is reduced.

43. The method of claim 37 wherein the biological medium is urine containing uric acid, and wherein the concentration of uric acid is to be determined.

44. The method of claim 37 wherein the biological medium is saliva containing alcohol, and wherein the concentration of alcohol is to be determined.

45. The method of claim 37 wherein the biological medium is blood containing cholesterol, and wherein the concentration of cholesterol is to be determined.

46. The method of claim 37 wherein the biological medium is human serum containing beta-hydroxy butyrate, and wherein the concentration of beta-hydroxy is to be determined.

47. A diagnostic device for the quantitative or qualitative determination of an organic analyte in a biological medium, which comprises:
in combination, support means for a dehydrogenase capable of oxidizing the organic analyte, NAD(P), a chromogen which produces a color change upon reduction by NAD(P)H in the presence of diaphorase, a non-chromogenic competing substrate which is irreversibly reducible by NAD(P)H in the presence of diaphorase, and diaphorase,
wherein the color change produced upon reduction of the chromogen occurs in a ratio of less than one molecule of dye per molecule of NAD(P)H.

48. The device of claim 47 wherein the organic analyte is selected from the group consisting of carbohydrates, polyalcohols and ketones and the biological medium is selected from the group consisting of blood, serum, saliva and urine.

49. The device of claim 47 wherein the diaphorase catalyzes the reduction of the competing substrate and the chromogen with similar efficiency.

50. The device of claim 47 wherein the analyte is selected from the group consisting of alcohol, glucose, ketone and lactic acid.

51. A test kit for colorimetric measurement of the amount of an organic analyte is solution wherein the analyte is capable of being oxidized in a NAD(P)-dependent dehydrogenase reaction to produce NAD(P)H, wherein the test kit comprises at least one reaction area means, containing NAD(P), a dehydrogenase capable of oxidizing the organic analyte, diaphorase, a chromogen which produces a color change upon irreversible reduction by NAD(P)H in the presence of diaphorase and a non-chromogenic competing substrate which is irreversibly reduced by NAD(P)H in the presence of diaphorase, wherein the amount of color produced upon reduction of the chromogen is less than that produced in the absence of the competing substrate and the color change occurs in a ratio of less than one molecule of dye per molecule of NAD(P)H produced, said color change being indicative of the concentration of the analyte to be determined.

52. The test kit of claim 51 which comprises two reaction area means, a first reaction area means containing the NAD(P) and the dehydrogenase and a second reaction area means containing the diaphorase, the chromogen and the non-chromogenic competing substrate.

53. The test kit of claim 52 which further comprises a known amount of reduced chromogen, reduced non-chromogenic competing substrate and oxidized organic analyte.

54. The test kit of claim 51 which comprises a collection means for oxidized analyte.

55. The test kit of claim 51 wherein the reactions are carried out in a liquid.

56. The test kit of claim 51 wherein the reactions are carried out on a solid medium.

57. The test kit of claim 51 wherein the affinity of the diaphorase for the competing substrate is greater than that for the chromogen, whereby the non-chromogenic competing substrate is reduced without production of color prior to reduction of the chromogen, and wherein color is produced upon subsequent reduction of the chromogen.

58. The kit of claim 51 wherein the diaphorase catalyzes the reduction of the non-chromogenic competing substrate and the chromogen with similar efficiency.

59. The test kit of claim 51, wherein the reaction area means comprises a test strip of absorbent material.

60. The test kit of claim 59 wherein the reaction area means is a multilayer test strip.

61. The test kit of claim 60 wherein the dehydrogenase and the NAD(P) are positioned in a first layer of the test strip and the diaphorase, the chromogen and the non-chromogenic competing substrate are positioned in at least one other layer, and wherein NAD(P)H produced in the first layer diffuses into at least one other layer for detection.

* * * * *

UNITED STATES PATENT AND TRADEMARK OFFICE
CERTIFICATE OF CORRECTION

PATENT NO. : 5,032,506

DATED : July 16, 1991

INVENTOR(S) : John L. Palmer et al.

It is certified that error appears in the above-identified patent and that said Letters Patent is hereby corrected as shown below:

Claim 14, col. 24, line 61, after "2-mercaptoethanol" delete --, --;

Claim 14, col. 24, line 63, after "1,4-benzoquinone" insert --,--;

Claim 51, col. 27, line 5, change "is" to --in--.

Signed and Sealed this

Twenty-seventh Day of October, 1992

*Attest:*

DOUGLAS B. COMER

*Attesting Officer*     *Acting Commissioner of Patents and Trademarks*